US006714712B2

(12) United States Patent
Bishop et al.

(10) Patent No.: US 6,714,712 B2
(45) Date of Patent: Mar. 30, 2004

(54) RADIATION CURABLE COATING COMPOSITION

(75) Inventors: Timothy E. Bishop, Algonquin, IL (US); Franciscus J. M. Derks, Heythuysen (NL); Anthony Tortorello, Elmhurst, IL (US)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 10/042,279

(22) Filed: Jan. 11, 2002

(65) Prior Publication Data

US 2002/0168164 A1 Nov. 14, 2002

Related U.S. Application Data

(60) Provisional application No. 60/260,672, filed on Jan. 11, 2001, and provisional application No. 60/265,308, filed on Feb. 1, 2001.

(51) Int. Cl.⁷ .............................. G02B 6/02; G02B 6/22; G02B 6/16; C07K 0/00
(52) U.S. Cl. .......................... 385/128; 260/18; 385/123
(58) Field of Search ............................ 385/128; 522/83, 522/92, 25

(56) References Cited

U.S. PATENT DOCUMENTS

| | | | | |
|---|---|---|---|---|
| 4,100,318 A | * | 7/1978 | McCann et al. | 428/159 |
| 4,112,017 A | | 9/1978 | Howard | 260/859 R |
| 4,164,486 A | | 8/1979 | Kudo et al. | 260/22 TN |
| 4,528,307 A | * | 7/1985 | Fuhr et al. | 522/83 |
| 4,885,332 A | * | 12/1989 | Bilkadi | 524/714 |
| 5,104,929 A | * | 4/1992 | Bilkadi | 524/847 |
| 5,128,387 A | * | 7/1992 | Shustack | 522/92 |
| 5,128,391 A | * | 7/1992 | Shustack | 522/92 |
| 5,146,531 A | | 9/1992 | Shustack | 385/128 |
| 5,629,354 A | * | 5/1997 | West et al. | 522/25 |
| 5,942,372 A | * | 8/1999 | West et al. | 430/281.1 |
| 6,011,078 A | | 1/2000 | Reich et al. | 522/86 |
| 6,099,415 A | * | 8/2000 | Lutz | 473/357 |

FOREIGN PATENT DOCUMENTS

| | | |
|---|---|---|
| BE | 814979 | 11/1974 |
| BE | 846356 | 3/1977 |
| DE | 2731085 | 1/1978 |
| DE | 2638867 | 3/1978 |
| DE | 2639667 | 3/1978 |
| DE | 2641662 | 3/1978 |
| DE | 2838691 | 3/1979 |
| DE | 3241264 | 5/1984 |
| DE | 3316593 | 11/1984 |
| DE | 3319013 | 11/1984 |
| DE | 3836370 | 5/1990 |
| DE | 40 07 519 | 9/1991 |
| DE | 4040290 | 7/1992 |
| DE | 41 26 860 | 2/1993 |
| DE | 4126860 | 2/1993 |
| DE | 196 02 071 | 6/1996 |
| DE | 196 00 136 | 7/1997 |
| DE | 196 16 984 | 10/1997 |
| EP | 2866 | 7/1979 |
| EP | 54105 | 6/1982 |
| EP | 87580 | 9/1983 |
| EP | 127766 | 12/1984 |
| EP | 144703 | 6/1985 |
| EP | 279303 | 8/1988 |
| EP | 350730 | 1/1990 |
| EP | 407826 | 1/1991 |
| EP | 508409 | 10/1992 |
| EP | 624609 | 11/1994 |
| EP | 680985 | 11/1995 |
| EP | 686621 | 12/1995 |
| EP | 739922 | 10/1996 |
| EP | 775687 | 11/1996 |
| EP | 874014 | 4/1998 |
| EP | 900778 | 8/1998 |
| EP | 933353 | 1/1999 |
| NL | 7707669 | 7/1977 |
| WO | 97 27253 | 7/1997 |
| WO | 97/46594 | 12/1997 |
| WO | 98/14500 | 4/1998 |
| WO | 98/18862 | 5/1998 |
| WO | 98/18874 | 5/1998 |
| WO | 98/56500 | 12/1998 |
| WO | 98 56846 | 12/1998 |
| WO | 99/21894 | 5/1999 |

OTHER PUBLICATIONS

Patent Abstracts of Japan, vol. 006, No. 177, Sep. 11, 1982, Abstract JP 57 092552.
Patent Abstracts of Japan, vol. 008, No. 237, Oct. 30, 1984, Abstract of JP 59 114504.
Patent Abstracts of Japan., vol. 010, No. 161, Jun. 10, 1986, Abstract of JP 61 014154.
Patent Abstracts of Japan, vol. 008, No. 225, Oct. 16, 1984, Abstract of JP 59 111952.

* cited by examiner

*Primary Examiner*—Brian Healy
*Assistant Examiner*—Tina M Lin
(74) *Attorney, Agent, or Firm*—Pillsbury Winthrop LLP

(57) ABSTRACT

The invention relates to a radiation-curable coating, ink or matrix composition comprising:
(A) a polyester (meth)acrylate oligomer comprising more than about 1 mole of diacid,
(B) optionally, a reactive diluent, and
(C) optionally, a photoinitiator,
wherein the composition when cured and aged at 85° C. and 85 % Relative Humidity for 10 days is hydrolytically stable to such an extent that the coating, ink or matrix maintains mechanical integrity. The invention further relates to said compositions for use as a primary coating composition, which, after cure, has a modulus of less than about 5 MPa, for use as a secondary coating or ink composition and for use as a matrix material, which, after cure, has a modulus of at least about 5 MPa. The invention also relates to a coated and optionally inked optical fiber and to an optical fiber ribbon comprising a coating, ink or matrix material as described above.

17 Claims, No Drawings

RADIATION CURABLE COATING COMPOSITION

This application claims the benefit of U.S. Provisional Application Nos. 60/260,672, tiled Jan. 11, 2001 and 60/265,308 filed Feb. 1, 2001. Both of the provisional applications are hereby incorporated in their entirety by reference.

FIELD OF THE INVENTION

The present invention relates to coated optical fibers and to radiation curable compositions, which are adaptable for use as a covering layer in optical fiber technology, such as a primary coating, secondary coating, upjacketing or tight-buffer coating, bundling material, ribbon matrix material, each of which can be colored or not, or ink composition for optical fibers.

BACKGROUND OF THE INVENTION

Glass optical fibers are provided with protective coatings immediately after spinning the molten glass. Generally, two coatings are applied, a primary coating of a relatively soft, flexible resin directly on the glass surface, and a harder resin, a secondary coating, on the primary coating. The individual fibers generally are combined in larger structures such as cables. Cables may comprise individual fibers, or fiber ribbon structures. The optical fiber ribbon generally is made from 2, 4, 6, 8 or 12 optical fibers, generally arranged in a plane, and bonded together with a so-called matrix material. Several ribbons can be bundled together using bundling materials. Further, individual fibers often are provided with a coloring or ink layer to be able to identify individual fibers. In certain cases, the individually coated fibers that have a thickness of about 250 μm are provided with a further coating layer to make a thicker and thereby more easy to handle fiber. Such a coating is denoted as an upjacketing coating. All of the materials presently in use for these applications are preferably radiation curable compositions.

In many of these compositions, use is made of a urethane oligomer having reactive termini and a polymer backbone. Further, the compositions generally comprise reactive diluents, photoinitiators to render the compositions UV-curable, and suitable additives.

As polymer backbone for the urethane oligomer, many materials have been suggested. In the synthesis of the oligomer backbone, polyols have been used such as hydrocarbon polyols, polyether polyols, polycarbonate polyols and polyester polyols. Polyester polyols are particularly attractive because of their commercial availability, oxidative stability and versatility to tailor the characteristics of the coating by tailoring the backbone. Polyester polyols used as the backbone polymer in a urethane acrylate oligomer are described for use in optical fiber coatings in e.g. U.S. Pat. No. 5,146,531 and EP-A-539030. However, polyester polyols in general are susceptible to hydrolysis.

Urethane-free polyester acrylate oligomers have also been used in radiation-curable coating compositions for optical glass fibers.

For example, JP-5792552 (Nitto Electric) discloses a coating material for optical glass fibers comprising a polyester di(meth)acrylate, the polyester backbone having an average molecular weight of 300 or more. The polyesters are synthesized by reacting saturated polybasic acids and polyalcohols by standard esterification reactions and polyester polyols are produced by using an excess of polyalcohols in this reaction. Next, the polyol is reacted with acrylic acid or methacrylic acid. The coating compositions disclosed in JP-5792552 typically contain said polyester di(meth)acrylate oligomer, a (meth) acrylate ester monomer, a radical photoinitiator and additives. This coating is used as a so-called single coating for optical glass fibers.

The disadvantage of the coatings disclosed in JP-5792552 is their susceptibility to hydrolysis. It appears that, after aging, the coating integrity is lost. Thus, the coated optical fiber will not be adequately protected from the environment, resulting in signal attenuation. Moreover, the single coatings disclosed in JP-5792552 appeared to not have the appropriate mechanical properties, such as modulus and Tg, necessary for low signal attenuation. Furthermore, the coatings of JP-5792552 appeared to show an insufficient cure speed.

From DE-A1-4126860 (Bayer), a matrix material for a three-fiber ribbon is known consisting of a polyester acrylate oligomer, 2-(N-butyl-carbamyl)-ethylacrylate as reactive diluent and 2-hydroxy-2-methyl-1-phenyl-propan-1-one as photoinitiator. The matrix material disclosed in DE-A1-4126860 appeared not to have the required mechanical properties. It appears that the modulus of the matrix material exemplified in DE-A1-4126860 is too low to be acceptable as a matrix material. Moreover, said matrix material appeared to show insufficient hydrolytic stability.

From JP-243227/1998 a liquid curable resin composition is known comprising a polyester acrylate oligomer which consists of a polyether diol endcapped with two diacids or anhydrides and terminated with hydroxy ethyl acrylate. However, the polyester acrylate disclosed and the resulting resin composition appeared to show insufficient hydrolytic stability.

It is an object of the present invention to provide a coating, ink or matrix composition comprising a polyester and/or alkyd (meth)acrylate oligomer having greater utility and better stability and which is adapted for use as a coating, composition or matrix material for an optical glass fiber.

It is a further object of the present invention to provide a primary coating, secondary coating, upjacketing coating, ink, matrix or bundling composition for an optical fiber comprising a polyester and/or alkyd (meth)acrylate oligomer having good mechanical properties.

It is a further object of the invention to obtain an optical fiber or optical fiber ribbon, or optical fiber cable comprising at least one of said coating, ink or matrix as defined above.

SUMMARY OF THE INVENTION

Surprisingly, one or more of the above objects can be obtained by the radiation-curable coating composition, ink composition or matrix material comprising a polyester and/or alkyd (meth)acrylate oligomer.

The present invention provides a radiation-curable coating, ink or matrix composition comprising:

(A) a polyester and/or alkyd (meth)acrylate oligomer comprising a polyacid residue or anhydride thereof,
(B) optionally, a reactive diluent, and
(C) optionally, a photoinitiator, wherein said composition when cured and aged under 85° C. and 85% Relative Humidity conditions for 10 days is hydrolytically stable to such an extent that the coating maintains mechanical integrity. Mechanical integrity means that the coating sample remains intact to such an extent that the coating sample can be measured in a DMA measurement as described in more detail in the description of test methods. Preferably, the coating composition does not fall apart when a sample thereof is prepared for the DMA-measurement. The term polyacid is used to refer to di- as well as polyacid.

Preferably, the polyester (meth)acrylate oligomer according to the present invention comprises more than about 1 mole of diacid.

In particular, the Mn, functionality and/or building blocks of said oligomer and/or the other components of the composition and/or the method of preparation of the oligomer and/or the curing conditions can be chosen such as to achieve the required hydrolytic stability.

The present invention further relates to said composition for use as an optical fiber primary coating having a modulus of about 5 MPa or less; for use as an optical fiber secondary coating or ink composition; and for use as an optical fiber matrix material having a modulus of at least about 5 MPa.

The present invention further provides a radiation-curable coating, ink or matrix composition comprising:

(A) a polyester and/or alkyd (meth)acrylate oligomer comprising a polyacid residue or anhydride thereof, (B) optionally, a reactive diluent, and (C) optionally, a photoinitiator, wherein said composition when cured and submitted to 200° C. for 40 minutes in a Thermogravimetric Analysis (TGA) measurement shows a weight loss of about 10% or less.

Preferably, the polyester (meth)acrylate oligomer according to the present invention comprises more than about 1 mole of diacid.

The present invention further relates to a coated optical fiber comprising a glass optical fiber having a primary coating, a secondary coating, upjacketing coating and optionally an ink composition applied thereon, and to an optical fiber ribbon comprising at least two of said coated and optionally inked optical fibers wherein at least one of said coating or composition is derived from a radiation-curable composition as described above. Detailed description of the invention For the sake of simplicity, the term "polyester (meth)acrylate" is further used to refer to polyester acrylate, polyester methacrylate, alkyd acrylate as well as alkyd methacrylate or to mixtures thereof, unless it is specifically stated otherwise. The term "(meth)acrylate" is used to refer to methacrylate and acrylate. Generally, acrylates are preferred over methacrylates because compositions having higher cure speeds can be obtained.

Alkyds are regarded as a type of polyester. An alkyd (meth)acrylate comprises an alkyd backbone derived from an alkyd resin and acrylate or methacrylate reactive end groups. Alkyd resins, or alkyds, are polyesters having a pendant ester group protruding off of a main polymer chain of ester linkages. The pendant group of the alkyd can be introduced by including a monofunctional carboxylic acid (monoacid) along with the ordinary components used to prepare a polyester.

Further, the terms "coating" and "coating composition" are used to refer to primary coatings, secondary coatings, bundling materials, ribbon matrix materials, upjacketing materials, each of which can be colored or not, or ink compositions for optical fibers, unless specifically stated otherwise.

According to a preferred embodiment of the present invention, the radiation-curable coating composition comprises:

(A) a polyester (meth)acrylate oligomer comprising a polyacid residue or anhydride thereof, (B) optionally, a reactive diluent, and (C) optionally, a photoinitiator, wherein said composition when cured and aged under 85° C. and 85% Relative Humidity conditions for 10 days shows a change in equilibrium modulus $E_o$ of about 30% or less.

Preferably, the change in equilibrium modulus $E_o$ after aging for 10 days is about 20% or less, more preferably about 15% or less, even more preferred about 10% or less, and most preferred about 7% or less. Preferably, the minimum final $E_o$ value reached is at least about 0.1 MPa, more preferred at least about 0.5 MPa.

Preferably, said coating when aged for 30 days at 85° C. and 85% Relative Humidity shows a change in equilibrium modulus $E_o$ of about 70% or less, preferably about 60% or less, more preferably about 50% or less, even more preferred about 40% or less, and most preferred about 30% or less. It is preferred that the final $E_o$ value reached is at least about 0.1 MPa.

Preferably, the polyester (meth)acrylate oligomer according to the present invention comprises more than about 1 mole of diacid.

According to a particularly preferred embodiment of the present invention the radiation curable coating composition when cured and when aged for 60 days at 85° C. and 85% Relative Humidity shows a change in equilibrium modulus $E_o$ of about 80% or less, preferably about 70% or less, more preferably about 60% or less, even more preferred about 50% or less, and most preferred about 30% or less. Further, when aged for 60 days at 85° C. and 85% Relative Humidity the coating preferably shows a change in Tg (Atan delta max) of less than 20° C., more preferably, less than 15° C., even more preferably less than 10° C., and most preferred less than 7° C. Preferably, when aged for 60 days at 85° C. and 85% Relative Humidity the coating shows a weight change of less than 5%, more preferably less than 2%, most preferred less than 1%.

At least one of the following measures can be taken to obtain the stable coating of the present invention, said measures relating to increasing the stability of the oligomer (A) and/or the stability of the radiation-curable composition, in particular the respective hydrolytic stabilities. A combination of several of the following measures is preferred to further improve the hydrolytic stability of the coating.

To obtain more hydrolytically and/or thermal resistant oligomers, the oligomer can be chosen by modifying its building blocks, for example by choosing more hydrolytically and/or thermal stable or more sterically hindered polybasic acid and/or alcohol building blocks. Oligomers having reduced acid values can be chosen as well. The amount of remaining acid in the polyester (meth)acrylate oligomer, such as, for example, the remaining (meth)acrylic acid and the remaining acid of the catalyst if applicable (i.e. if used as the catalyst in the (meth)acrylation step during the synthesis of the polyester (meth)acrylate) can be quantified by the acid value of the polyester (meth)acrylate oligomer (further defined as the resin). The acid value of the resin is a measure of the free carboxylic acids content of a resin and is expressed as the number of milligrams of potassium hydroxide required to neutralize the free carboxylic acids in one gram of the resin. A weighed quantity of the resin is dissolved in a solvent such as toluene or tetrahydrofuran (THF) together with neutralized ethyl alcohol and titrated with carbonate-free decinormal potassium hydroxide solution to a phenolphthalein end point. It is possible to determine the acid value potentiometrically as described further below under the test methods section. The acid value can be expressed by formula (1):

$$\text{Acid value} = \frac{(56.1 \times \text{mL KOH} \times \text{normality})}{\text{mass of resin (g)}} \text{ (mg KOH/g resin)} \quad (1)$$

According to a preferred embodiment of the present invention, the acid value is below about 20 mg KOH/g or less, more preferred below about 15 mg KOH/g or less, particularly preferred about 10 mg KOH/g or less, even more preferred about 5 mg KOH/g or less, and most preferred the resin is completely neutralized (acid value<0.1 mg KOH/g resin). Oligomers having a low acid value show improved hydrolytic stability. Therefore, according to a preferred aspect of the present invention, after synthesis of the polyester (meth)acrylate, the oligomer is further washed or neutralized, to remove the excess acid, or both.

Polyester (meth)acrylates having a relatively low amount of ester linkages are also preferred. Preferably, the polyester (meth)acrylates contain less than about 10 ester linkages per 1000 Mw of the oligomer, more preferably, less than about 8, even more preferably less than about 7, particularly preferred less than about 6.5 and most preferred less than about 6. Further, it is preferred to have ester levels (total ester linkages per oligomer %) of less than about 10, more preferred less than about 7, even more preferred less than about 5. Of course, the allowed ester levels do also depend on other factors, such as the type of ester linkage(s), the catalyst residues, and the like. Also preferred are hydrophobic polyester (meth)acrylate oligomers and hydrophobic radiation-curable compositions. It is thus preferred to have more apolar compounds present in the composition of the present invention to achieve a higher hydrophobicity.

Further, it is preferred to optimize the functionality of the various components of the radiation-curable composition as such that the composition, when cured, forms a good network.

According to one particular embodiment, the radiation-curable coating, ink or matrix composition according to the present invention comprises:

(A) a polyester (meth)acrylate oligomer comprising a polyacid residue or anhydride thereof, (B) optionally, a reactive diluent, and (C) optionally, a photoinitiator, wherein said composition when cured and submitted to 200° C. for 40 minutes in a Thermogravimetric Analysis (TGA) measurement shows a weight loss of about 10% or less. Preferably, the weight loss is about 7% or less, more preferably, about 5% or less. Preferably, the polyester (meth) acrylate oligomer according to the present invention comprises more than about 1 mole of diacid.

Incompletely cured coatings can be one of the reasons for achieving unsatisfactorily TGA weight loss values. Therefore, the coating composition of the present invention comprising a polyester (meth)acrylate is formulated as such that sufficient curing is achieved. The curing is measured by FTIR, as the % RAU (% Reacted Acrylate Unsaturation, see description test method). Preferably, the coating composition, when cured with an UV-lamp having a certain energy output as defined in the test method, has a ratio of the % RAU after 0.2 sec exposure to the % RAU after 10 sec exposure of at least about 25%, more preferably, at least about 30%, even more preferred, at least about 35%, most preferred, at least about 40%.

For the primary coating of the present invention, the % RAU at 10 seconds exposure as defined above preferably is at least about 90%, more preferably, at least about 94%, even more preferred, at least about 96%, most preferred, at least about 98%. For the secondary coating, the ink composition and the matrix material of the present invention, the % RAU at 10 seconds exposure as defined above preferably is at least about 60%, more preferably, at least about 65%, even more preferred, at least about 70%, most preferred, at least about 75%.

Preferably, the radiation-curable coating composition according to the present invention, in the absence of an additive or anti-oxidant, when cured and submitted to Differential Scanning Calorimetry (DSC) shows an onset of oxidation temperature (OIT) of at least about 217° C. Preferably, the OIT-temperature is at least about 220° C., more preferably, at least about 225° C., even more preferred, at least about 230° C. The higher the OIT-temperature, the greater the oxidative stability of the coating is.

The cured coatings of the present invention have a further advantage of showing good durability in hot alkaline solution. The durability of the cured film is evaluated as the % weight loss or the change in Young's modulus, after being soaked for 1 week in hot alkaline solution (water of pH 13 at 80° C.). The coatings of the present invention preferably show a % weight loss after 1 week in hot alkaline solution of less than about 10%, more preferred, less than about 9%, particularly preferred, less than about 7%. After 1 week in hot alkaline solution, the coatings of the present invention preferably show a change in Young's modulus of less than about 9%, more preferred, less than about 8%, particularly preferred, less than about 6%, and most preferred less than about 5%.

The cured coatings of the present invention, when aged at 85° C. under dry conditions for 60 days preferably shows a change in equilibrium modulus $E_o$ of about 30% or less, more preferably about 20% or less, and most preferred about 10% or less.

The cured coatings of the present invention, when aged under low intensity fluorescent light in dry conditions for 60 days preferably shows a change in equilibrium modulus $E_o$ of about 60% or less, more preferably about 50% or less, even more preferably about 40% or less, particularly preferred about 30% or less, and most preferred about 15% or less.

The polyester backbone according to the invention can be derived from (i) saturated or unsaturated polybasic acids and (ii) polyalcohols to obtain polyester polyols. Saturated polybasic acids and polyalcohols are preferred. The polyester polyol is then further reacted with (iii) acrylic or methacrylic acid or its ester derivatives to obtain the polyester (meth) acrylate.

A preferred polyester (meth)acrylate, in particular for the higher modulus coatings (the so-called hard coatings), such as the secondary coatings, inks and matrix materials, contains on average at least about 2.5 mol of diacid per oligomer.

The polyester or alkyd can be made by any method. Preferably, alkyd resins can be prepared by condensation reactions of polyfunctional alcohols (hereafter referred to as polyols), polyfunctional carboxylic acids (hereafter referred to as polyacids), and oils or fatty acids derived from the oils. The oil can be a natural oil (which consists of an ester, e.g., a triester of glycerol and fatty acids). For example, a polyol/fatty acid mixture can be prepared in situ by alcoholysis of a naturally derived oil or by direct esterification of a polyol with a naturally derived long chain fatty acid. The resulting product from either of these reactions can then be polymerized with other polyols and polyacids (e.g., diols and diacids) as in conventional polyesterification. More preferably, the alkyd is prepared by alcoholysis of a naturally derived oil, preferably one with a low degree of unsaturation.

(i) As the polybasic acids for the polyester and/or alkyd (meth)acrylates, polyfunctional carboxylic acids and the corresponding anhydrides can be used. Preferably, aromatic or aliphatic dibasic carboxylic acids and the corresponding anhydrides are used such as phthalic acid or anhydride, isophthalic acid, terephthalic acid, maleic acid or anhydride, fumaric acid, itaconic acid or anhydride, adipic acid, glutaric acid, azelaic acid, sebacic acid, citric acid, trimellitic acid or anhydride, pyromellitic acid or dianhydride, dodecane dicarboxylic acid, dodecane dioic acid, cyclohexane dicarboxylic acid, tetrahydrophthalic acid anhydride, methylene tetrahydrophthalic acid or anhydride, hexahydrophthalic acid anhydride, succinic acid or acid anhydrides thereof or lower alkyl esters thereof, dimer-fatty acid and the like. Mixtures of said acids may also be used.

Dimer acids (and esters thereof) are a well known commercially available class of dicarboxylic acids (or esters). They are normally prepared by dimerizing unsaturated long chain aliphatic monocarboxylic acids, usually of 13 to 22 carbon atoms, or their esters (e.g. alkyl esters). The dimerization is thought by those in the art to proceed by possible mechanisms which include Diels-Alder, free radical, and carbonium ion mechanisms. The dimer acid material will usually contain 26 to 44 carbon atoms. Particularly, examples include dimer acids (or esters) derived from C-18 and C-22 unsaturated monocarboxylic acids (or esters) which will yield, respectively, C-36 and C-44 dimer acids (or esters). Dimer acids derived from C-18 unsaturated acids, which include acids such as linoleic and linolenic are particularly well known (yielding C-36 dimer acids).

The dimer acid products will normally also contain a proportion of trimer acids (e.g. C-54 acids when using C-18 starting acids), possibly even higher oligomers and also small amounts of the monomer acids. Several different grades of dimer acids are available from commercial sources and these differ from each other primarily in the amount of monobasic and trimer acid fractions and the degree of unsaturation.

Usually the dimer acid (or ester) products as initially formed are unsaturated which could possibly be detrimental to their oxidative stability by providing sites for crosslinking or degradation, and so resulting in changes in the physical properties of the coating films with time. It is therefore preferable (although not essential) to use dimer acid products which have been hydrogenated to remove a substantial proportion of the unreacted double bonds.

Herein the term "dimer acid" is used to collectively convey both the diacid material itself or ester-forming derivatives thereof (such as lower alkyl esters) which would act as an acid component in polyester synthesis and includes (if present) any trimer or monomer.

In particular preferred are adipic acid, isophthalic acid, terephthalic acid, and dimer-fatty acid or mixtures thereof. Also preferred are tetrahydrophthalic acid anhydride, hexahydrophthalic acid anhydride, 1,4-cyclohexane dicarboxylic acid (CHDA), succinic acid or mixtures thereof. Polyester (meth)acrylates based on these acids generally show good hydrolytic stability.

(ii) As the polyalcohols, a wide range of well-known polyalcohols can be used. Suitable polyalcohols comprise 2–10 alcohol groups, preferably 2–4 alcohol groups. Suitable examples include 1,2-propanediol, 1,3-propanediol, 1,4-butanediol, 1,2-butanediol, 1,3-butanediol, 1,5-pentanediol, 1,6-hexanediol, 1,9-nonanediol, ethylene glycol, diethylene glycol, triethylene glycol, polyethylene glycol, dipropylene glycol, polypropylene glycol, glycerol, trimethylol ethane, trimethylol propane, neopentyl glycol, pentaerythritol, dipentaerythritol, sorbitol, 2-methyl-1, 3-propane diol, 2,2-dimethyl-1, 3-propanediol, 2-ethyl-1, 3-propanediol, 2,2-diethyl-1,3-propanediol, 2-propyl-2-methyl-1,3-propanediol, 2-propyl-2-ethyl-1,3-propanediol, 2-butyl-2-ethyl-1,3-propanediol (BEPD), hydroxy pivaloyl hydroxy pivalate (HPHP), 2-cyclohexyl-2-methyl-1,3-propanediol, 2-phenyl-2-methyl-1.3-propanediol, 1,4-cyclohexanediol, 2,4-diethyl-1,5-pentane diol, or alkoxylated derivatives of all the above polyalcohols, such as preferably, ethoxylated and propoxylated derivatives thereof, ethoxylated bisphenol-A having 2–12 ethylene oxide units, propoxylated bisphenol-A having 2–12 propylene oxide units, reduced dimer acids, and the like. Reduced dimer acids are the hydrogenated analogs of dimer acids as described above, thus are diols, and are preferred as building blocks in the polyester (meth)acrylates of the present invention, in particular when used in primary coating compositions. Advantageous of the reduced dimer acids is their relative apolar character, the reduced ester content of the resulting polyester (meth)acrylate and their low Tg. Examples of C36 reduced dimer acids are Pripol 2033 (supplied by Uniqema) and Speziol C36/2 (supplied by Cognis). These diol components can be used in admixture.

Preferred are ethoxylated bisphenol-A, propoxylated bisphenol-A, neopentyl glycol (NPG), 2-butyl-2-ethyl-1,3-propane diol (BEPD), 2-methyl-1,3-propanediol (MPD), hydroxy pivaloyl hydroxy pivalate (HPHP), hydrogenated analogs of dimer acids, 2,4-diethyl-1,5-pentane diol or mixtures thereof. Particularly preferred are NPG, BEPD, and 2,4-diethyl-1,5-pentane diol because the oligomer (A) based on these alcohols show remarkably good hydrolytic stability. It is particularly preferred to use alcohols of which the β-position with respect to the hydroxyl group is substituted, more preferably, there is no hydrogen present on the β-position.

For the alkyds, the monoacid can be any monocarboxylic acid having between 4 and 28 carbon atoms. Preferably, the monoacid is a fatty acid, more preferably a long chain monoacid. A long chain monoacid, or long chain fatty acid, is characterized as having between 12 and 28 carbon atoms in their chain; more preferably, between 12 and 24 carbon atoms. Most fatty acids have 18 carbon atoms in their chain, but also a higher number of carbon atoms in naturally derived oils is possible. For example, $C_{22}$ acid, erucic acid (docosenoic acid), is found in some varieties of rapeseed oil. Preferably, naturally derived fatty acids or oils from which fatty acids are derived, as known to those skilled in the art, are fatty acids or oils originating from vegetable or animal sources.

The fatty acids or oils suitable in the alkyd backbones according to the present invention can be unsaturated or saturated. Preferably, the fatty acids or oils have a low degree of unsaturation, as defined hereunder. Examples of unsaturated oils or fatty acids (derived from the oils) include castor oil, corn oil, cottonseed oil, rapeseed oil, low eruric rapeseed oil, hempseed oil, kapok oil, linseed oil, wild mustard, oiticica oil, olive oil, palm oil, peanut oil, perilla oil, poppyseed oil, tobaccoseed oil, argentine rapeseed oil, rubberseed oil, safflower oil, sesame oil, soybean oil, sugarcane oil, sunflower oil, tall oil, teaseed oil, tung oil, black walnut oil, or mixtures thereof, and the like.

Examples of fatty acids/oils having a low degree of unsaturation include coconut oil, babassu oil, Chinese tallow oil, ouri-curl oil, palm kernel oil, caprylic acid, caproic acid, capric acid, coconut fatty acid, lauric acid, myristic acid, palmitic acid, stearic acid, and the like or mixtures thereof, fatty acids derived from the oils, as well as the hydrogenated form of unsaturated oils and fatty acids derived from the oils, such as castor oil, corn oil, cottonseed oil, rapeseed oil, low eruric rapeseed oil, hempseed oil, kapok oil, linseed oil, wild mustard, oiticica oil, olive oil, palm oil, peanut oil, perilla oil, poppyseed oil, tobaccoseed oil, argentine rapeseed oil, rubberseed oil, safflower oil, sesame oil, soybean oil, sugarcane oil, sunflower oil, tall oil, teaseed oil, tung oil, black walnut oil, or mixtures thereof, and the like.

(iii) The (meth)acrylation of the polyester polyol is finally carried out with acrylic or methacrylic acid or its ester derivatives. With the term (meth)acrylic acid is meant a compound according to the following formula (2):

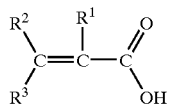

(2)

wherein: $R^1$, $R^2$, $R^3$ can be the same or different and are chosen from hydrogen, C1–C12 alkyl or alkaryl, C6–C12 aryl or arylalkyl or halogen, or —$CH_2$-X, wherein X can be chosen from the list: halogen, hydroxy or alkoxy with 1–6 carbon atoms. For example when $R^1$, $R^2$ and $R^3$ are all hydrogen the compound is acrylic acid, when $R^1$ and $R^2$ are hydrogen and $R^3$ is methyl, the compound is crotonic acid, when $R^2$ and $R^3$ are hydrogen and R' is methyl, the compound is methacrylic acid, when $R^1$ and $R^2$ are hydrogen and $R^3$ is phenyl, the compound is cinnamic acid.

Polyester (meth)acrylates are prepared by the condensation of (meth)acrylic acid with hydroxyl groups on a polyol or a polyester backbone or hydroxy (meth)acrylate with residual acid groups on a polyester structure. In some cases, an organic solvent may be required in the preparation to azeotropically aid the removal of water from the reaction. This can be followed by vacuum distillation of the solvent. The synthesis can be carried out in a 1-step, a 2- or more-step process.

In the 1-step process, the acid component (i), alcohol component (ii), (meth)acrylic acid (iii) and catalyst are all charged together in a reactor in air. The reaction can be carried out at a temperature ranging from about 80 to 150° C., preferably, about 100 to 140° C., more preferably about 120 to 130° C., at atmospheric or reduced pressure. As a catalyst, organic acid and inorganic acid catalysts are effective. The catalyst can also have a functional group by which it can be or is, incorporated into a polymer or preferably, into the ester of (meth)acrylic acid e.g. a sulfonic acid functional polymer, a phosphoric acid functional polymer, and the like. Preferably, the catalyst is a strong acid (having a pKa value of about 2 or less, determined at 25° C. in water). As organic acid catalysts, alkyl sulfonic acids such as methane sulfonic acid, aryl sulfonic acids, such as p-toluene sulfonic acid, benzene sulfonic acid, styrene sulfonic acid and the like can be given. As inorganic catalysts, sulfuric acid, the mono-ester of sulfuric acid, phosphoric acid, the mono-ester of phosphoric acid and the like can be given. Catalysts such as p-toluene sulfonic acid are preferred due to their high effectiveness at the relatively low temperatures at which the (meth)acrylation step is carried out.

The concentration of the catalyst in the reaction mixture generally lies between 0.1–10 wt. %, preferably, 0.2–7 wt. %, more preferably, 0.5–5 wt. %, and most preferred, 0.7–3 wt. % (based on the total weight). When polymeric catalysts are used the range 0.1–50 wt % applies, preferably 0.5–40 wt. %, more preferably, 1.0–30 wt. %.

If a solvent is present, the solvent preferably is toluene, heptane, xylene, benzene or the like, more preferably, toluene. The water is then removed azeotropically. The end of the reaction is followed by monitoring the acid value (as described above) or the hydroxyl value. The hydroxyl value is a measure of the amount of hydroxyl groups, measured by titrating back the reaction product of the polyester with acetic anhydride, and is expressed as given by formula (3):

$$\text{Hydroxyl value} = \frac{\text{the number of mg of potassium hydroxide (KOH)}}{\text{mass of resin or polymer (g)}} \quad (3)$$

The reaction can also be monitored by NMR. The reaction time generally is between about 1 to 24 hours, preferably, between about 1 to 16 hours, more preferably between about 2 to 13 hours, and particularly preferred between about 5 and 12 hours. If a solvent is present, it is preferably vacuum distilled together with any unreacted (meth)acrylic acid.

According to a preferred embodiment of the present invention the polyester (meth)acrylate is prepared according to the 2-steps synthesis process, in particular in case of bad solubility of one of the components, e.g. one of the acids. During the first step of the 2-steps process, the polyester polyol is prepared by esterification of the acid (i) and the alcohol (ii) components at a temperature in the range of about 150–250° C., preferably 160–240° C., more preferred 180–230° C., preferably under nitrogen atmosphere. A solvent may also be present as discussed above. Preferably, the reaction is carried out under pressure, more preferably, at a pressure of about 10 bar or less, particularly preferred, at a pressure of about 6 bar or less. Generally, excess alcohol component (ii) is used in comparison with the acid component (i) to yield hydroxyl functional compounds or oligomers. As an esterification catalyst in step 1, organic acid, inorganic acid and metal catalysts are effective. Of these, organic acid catalysts and metal catalysts are preferred because of a high purity of the product and their effectiveness as a catalyst. As organic acid catalysts, alkyl sulfonic acids, such as methane sulfonic acid, aryl sulfonic acids, such as p-toluene sulfonic acid and benzene sulfonic acid, and the like can be given. As inorganic catalyst, sulfuric acid, phosphoric acid, and the like can be given. As metal catalysts, tetra-isopropyl titanate, tetra-phenyl titanate, hydroxy titanium stearate, tetra-stearyl titanate, tetraethyl zirconate, tetra butoxy titannate (($BuO)_4Ti$, dibutyl tin oxide ($Bu_2$—SnO), butyl stannic acid (BuSnOOH), butyl tin chloro dihydroxide (BuSnCl(OH)$_2$)), and the like can be given. P-toluene sulfonic acid is particularly preferred because it is a highly effective catalyst and because of it's low cost. Particularly preferred are further butyl stannic acid and butyl tin chloro dihydroxide since only a small amount of the catalyst is needed to achieve a relatively high reactivity, in particular at the high temperatures of the first step reaction.

The second step of the 2-steps process, the (meth)acrylation of the polyester diol of step 1 takes place under the same reaction conditions, such as temperature and reaction time, as described for the 1-step process above. The reaction is preferably carried out (with air purge) by the addition of (meth)acrylic acid in a solvent, such as toluene, in the presence of a catalyst and an inhibition system to stabilize the (meth)acrylic unsaturation.

The (meth)acrylation reaction is preferably carried out until the hydroxyl conversion, as followed by NMR analysis, is completed for more than about 50%, more preferably, more than about 60%, particularly preferred, more than about 70%, even more preferred, more than about 85%, and most preferred more than about 95%. If reactants having relatively high functionality are used, only a lower hydroxyl conversion is required. In particular for secondary, ink and matrix type coatings, a OH-conversion of the polyester (meth)acrylate oligomer of at least about 95% was found to be preferred to maintain a good balance of mechanical properties and economy of manufacture. Lower degrees of OH-conversion tend to result in coatings having a relatively lower modulus and higher elongation, whereas Tg, cure speed and hydrolytic stability seem to remain relatively unaffected.

Preferably, the (meth)acrylation reaction is carried out until the (meth)acrylic acid conversion is completed for more than about 50%, more preferably, more than about 60%, even more preferably more than about 80%, particularly preferred more than about 90%, and most preferred more than about 95%.

To inhibit polymerization of the (meth)acrylic acid, an inhibition system can be added in the 1-step as well as in the 2-step process. Examples of suitable inhibition systems are hydroquinone, derivatives of hydroquinone, such as methylether hydroquinone, 2,5-dibutyl hydroquinone (DBH), and the like, nitrobenzenes, phenothiazines, and the like. Of these, 2,5-dibutyl hydroquinone (DBH) is preferred since a relatively low discoloration of the final oligomer can be achieved.

Stabilizers can further be used in the process, in particular color stabilizers, such as, for example, trisnonyl phenol phosphite (TNPP), trisphenol phosphite (TPP), and the like.

It is also preferred according to the present invention to further wash or neutralize the obtained polyester (meth) acrylate. Washing with organic aqueous base solution can be carried out till a neutral solution is obtained. According to a particularly preferred embodiment of the present invention, after the polyester (meth)acrylate has been synthesized, it is further neutralized by using epoxides, oxetanes, orthoesters, amines, or the like. The "neutralizing" step can be defined as the step in which the acid value of the resin is being reduced. Preferably, the neutralizing step comprises reacting free acid groups with one or more compounds wherein at least one compound forms with at least said acidic (trans)esterification catalyst an ester compound not having a p-hydroxy group or an amid compound.

Said at least one compound that reacts with the free acid groups is further referred to as the neutralizing compound. The neutralizing system is further defined as comprising said at least one neutralizing compound according to the present invention and—optionally—one or more other compounds (that can react with free acid groups). Said other compounds can be a β-hydroxy forming compound (such as an epoxide), an amine, a carbodiimide compound or any mixture thereof.

The neutralizing step can also be catalyzed, if required, by adding a neutralizing catalyst.

Free acid groups can originate from one or more of the following acid groups remaining in the resin after the synthesis step: free catalyst acid, free (meth)acrylic acid groups, and/or free carboxylic acid groups.

According to one embodiment, the neutralizing compound reacts with free acid groups originating from the free catalyst acid, free (meth)acrylic acid groups, and free carboxylic acid groups.

According to another preferred embodiment, the neutralizing compound according to the present invention reacts predominantly with free catalyst acid.

When more than one compound reacts with the free acid groups, the compounds can all be neutralizing compounds according to the present invention or the compounds can consist partly of neutralizing compound(s) and partly of said other compound(s).

When a β-hydroxy forming compound (such as an epoxide), an amine compound, a carbodiimide compound or any mixture thereof is present (further defined as "the other compound(s)"), said other compound(s) can be part of the neutralizing system from the beginning or—which is preferred—said other compound(s) are added only after the strong catalyst acid has been neutralized with the neutralizing compound according to the present invention.

Surprisingly, the polyester (meth)acrylate as neutralized according to the process of the present invention is found to be hydrolytically stable and does not turn turbid over time.

The ester or amid compound formed between the catalyst and the neutralizing compound as present in the polyester (meth)acrylate resin is a hydrolytically stable compound when the resin is stored in an open jar in an oven at 80° C. Preferably, the acid value of the resin does not substantially increase when stored in an open jar in an oven at 80° C. for at least 1 day, preferably, at least 2 days, more preferred, at least 4 days, particularly preferred, at least 1 week, and most preferred, at least 8 weeks.

Said at least one neutralizing compound can be selected from the group consisting of cyclic ethers, including 4-membered cyclic ethers such as oxetanes and derivatives, 1,2-dioxetanes, 1,3-dioxetanes; 5-membered cyclic ethers, such as dioxelanes, dihydrofuran, and the like; 6-membered cyclic ethers, such as dioxane and its derivatives, dihydropyran. Other suitable neutralizing compounds are orthoesters, esters and lactones, alcohols, carbonates and cyclic carbonates, acetoacetates, chloroformates, chlorosulfites, orthoborates, dialkyl sulfites, urea's, such as N,N'-(bis-2-hydroxyethyl) urea, silyl compounds, such as bis (trimethylsilyl) sulfate, siloxane compounds, such as octamethyl cyclo tetrasiloxane, diazo compounds, such as diazomethane and diazomethyl propylketone, isonitriles, such as phenyl isocyanide, phosphites, such as trialkyl or triaryl phosphites, phosphates, such as trialkyl or triaryl phosphates, phosphonates, such as diethylacetyl phosphonate, tin compounds, such as dibutyltinoxide. Further suitable neutralizing compounds are unsaturated compounds, such as vinyl ethers and cyclic vinyl ethers, allyl ethers, styrenes, olefins and cyclic olefins, maleates, fumarates, acrylates, methacrylates. Other suitable neutralizing compounds are oxazolines and isocyanates.

Preferred neutralizing compounds are chosen from the group consisting of a cyclic ether, an ortho-ester, an ester, a lactone, an alcohol, a carbonate, an unsaturated compound, or any mixture thereof.

More preferred, the neutralizing compound that reacts with the acidic esterification catalyst is selected from the group consisting of an oxetane compound, an ortho-ester compound, an alcohol compound, or a mixture of two or more thereof. The oxetane and ortho-ester compounds are preferred because they react relatively fast and quantitatively with the acidic catalyst and therefore, do not require long reaction times or high excess amounts. Ortho-ester compounds are preferred because they are readily available and relatively cheap.

Particularly preferred are the oxetane compounds, because substantially no side products are formed in the ester formation.

An oxetane compound or derivative can be defined by the following formula (4):

(4)

wherein X, Y and Z can be the same or different and can be a CR$_2$-group, a carbonyl (C=O), a heteroatom containing group (preferably, oxygen, nitrogen, —NR, phosphor —PR or P(=O)R), sulfur, or the like. The R groups can be the same or different and can be chosen from the group consisting of hydrogen, methyl, ethyl, propyl, butyl, and the like; halogenated alkyl, such as chloroalkyl (preferably, chloromethyl, chloroethyl), bromoalkyl (preferably, bromomethyl, bromoethyl), fluoroalkyl, and iodoalkyl; hydroxyalkyl, such as hydroxymethyl, and hydroxyethyl, and the like. An oligomeric or polymeric compound containing an oxetane moiety (4) can also be suitably used as neutralizing agent in the present invention.

The oxetane compound generally has a Mw of at least 58, preferably at least about 70, more preferred, at least about 101, even more preferred, at least about 115, and most preferred, at least about 129. The Mw of the oxetane compound is preferably less than about 10,000, more preferably, less than about 8,000.

Suitable examples of an oxetane compound (4) are oxetane, 3,3-dimethyl-oxetane, 3-bromoethyl-3-methyl-oxetane, 3-chloroethyl-3-methyl-oxetane, 3,3-dichloroethyl-oxetane, 3-ethyl-3-hydroxymethyl-oxetane, such as Cyracure® UVR6000, 3-methyl-3-hydroxymethyl-oxetane, 1,4-bis(3-ethyl-3-oxetanyl) methoxy, 3-ethyl-3-phenoxymethyl-oxetane, bis{[1-ethyl(3-oxetanyl)]methyl} ether, 3-ethyl-3-[(2-ethylhexyloxy)methyl] oxetane, 3-ethyl-[(tri-ethoxysilylpropoxy)methyl] oxetane, oxetanyl-silsesquioxane, and 3-methyl-3-hydroxymethyl-oxetane acrylate ester, and derivatives thereof, 1,2-dioxetanes, 1,3-dioxetanes, and the like, and mixtures of two or more of the above.

An ortho-ester compound or derivative can be defined by the following formula (5):

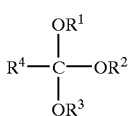

(5)

wherein each of R$^1$ to R$^3$ can be alkyl, cycloalkyl, aryl, and the like. Further, each of R$^1$, R$^2$ or R$^3$ can link to each other to form cycles with each other. R$^4$ can be hydrogen, alkyl, cycloalkyl, aryl, and the like. Alkyl can be methyl, ethyl, propyl, butyl, and the like. If R$^1$ is hydrogen, the ortho-ester compound is an ortho-formate compound. If R$^4$ is methyl, the compound is an ortho-acetate compound. An oligomeric or polymeric compound containing the above ortho-ester moiety (5) can also be suitably used as neutralizing agent in the present invention.

The ortho-ester compound generally has a Mw of at least 106, preferably, at least about 118, more preferred, at least about 200. The Mw of the ortho-ester compound is preferably less than about 10,000 more preferably, less than about 8,000. Examples of an ortho-ester compound are trialkyl ortho formate, such as trimethyl ortho formate, and trialkyl ortho acetates, such as trimethyl ortho acetate.

As the alcohol neutralizing compound, well-known mono alcohols can be used, such as methanol, ethanol, and the like; alkoxylated alkyl-substituted phenol derivatives, such as ethoxylated and propoxylated nonylphenol, alkoxylated unsubstituted phenol derivatives, isodecylalcohol, laurylalcohol, isobornylalcohol, and the like.

Further, a wide range of well-known polyalcohols, preferably diols, can be used as the alcohol neutralizing compound. Preferred alcohols as neutralizing agents are diols having the second hydroxy group in the γ-position, paticularly preferred are 1,3-diols, neopentyl glycol (NPG), 2-butyl-2-ethyl-1,3-propane diol (BEPD), trimethyloipropane (TMP), pentaerythritol (PET), monoesters therefrom, or any mixture thereof.

Other preferred alcohols as neutralizing agent are monoesters of diols, preferably diols having a second hydroxy in the β- or γ-position towards the first hydroxy.

Preferably, at least 10% of the acidic catalyst is being neutralized, more preferably, at least 20%, particularly preferred, at least 30%, even more preferred, at least 50%, and most preferred, the catalyst is substantially completely reacted away.

It is more preferred to use the neutralizing compound in such an amount that the amount of acidic catalyst as used in the synthesis is fully neutralized, preferably by using a small excess of neutralizing compound compared to the amount of acidic catalyst as added in the synthesis.

The neutralizing system (preferably the neutralizing compound) is preferably added in an amount of about 300 mol % or less relative to the total mol % of acid groups in the resin, more preferably, about 200 mol % or less, even more preferred, about 150 mol % or less, particularly preferred, about 120 mol % or less. Relative to the total mol % of acid catalyst in the resin, the oxetane or ortho-ester compound is preferably added in an amount of about 150 mol % or less, more preferably, about 120 mol % or less, particularly preferred, about 105 mol % or less.

According to one preferred embodiment, the neutralizing compound of the present invention or a mixture thereof reacts predominantly with strong acid having a pKa value of about 2 or less, including the catalyst acid. The weak acid having a pKa-value of more than about 2 is then neutralized by using the same or another neutralizing compound (or mixture) according to the present invention, or by using a β-hydroxy forming compound (for example an epoxide, such as glycidyl methacrylate, cyclohexene oxide, bisphenol-A-epoxides, and the like), an amine (such as dimethyl amino ethyl acrylate, dimethyl amino propyl acrylate, and the like), a carbodiimide or any mixture thereof. More preferred, after the strong acid has been neutralized with the neutralizing compound of the present invention, the weak acid is further reacted with a β-hydroxy forming compound (such as an epoxide), an amine, or a carbodiimide since these compounds are relatively cheap. Another preferred option is to initially add as the neutralizing system at least one of the neutralizing compounds of the present invention (preferably, the oxetane, ortho-ester or alcohol compound) in a mixture with an epoxide or amine compound, preferably in a mixture with an epoxide compound.

Optionally, any acid remaining after the neutralizing step according to the present invention can further be removed by different methods, such as by washing out, for example with aqueous base, extraction, distillation, further neutralization, or complexation with solid base. It is preferred to remove any remaining solvent and/or any remaining (carboxylic) acids by vacuum distillation under air purge. Said vacuum distillation is preferably carried out at temperatures in the range of about 100–180° C., more preferred in the range of about 120–160° C., even more preferred in the range of about 130–150° C. Further, said vacuum distillation is preferably carried out at pressures of less than about 0.5 bar, more preferred less than about 0.1 bar, even more preferred less than about 0.01 bar, particularly preferred around 10 mbar and preferably takes place, between about 15 minutes to about 5 hours, more preferred between about 30 minutes to about 4 hours, even more preferred between about 1 to 3 hours.

Further, suitable polyester (meth)acrylates according to the present invention that are commercially available include CN-2201 (chlorinated polyester acrylate), CN-2202 (chlorinated polyester acrylate), CN-292 and CN-2251 (all supplied by Sartomer), LR-8800 and PE-55F (both supplied by BASF), Actilane 505 and Actilane 579 (both supplied by Akzo Nobel).

The number average molecular weight Mn, functionality and building blocks of the polyester (meth)acrylate oligomer (A) affect the mechanical properties such as Tg and will thus be chosen in such a way as to obtain acceptable primary, secondary, ink or matrix properties. The functionality of the oligomer and reactive diluents has been found to have an influence on the stability, in particular the hydrolytic stability of the final composition.

The polyester (meth)acrylate oligomer, when used in a primary coating composition, preferably has a number average molecular weight (further called Mn) of at least about 1,000, more preferably, at least about 1,500, even more preferred, at least about 2,000. Preferably, its Mn is about 20,000 or less, more preferably, about 15,000 or less, even more preferred, about 10,000 or less, and most preferred, about 6,000 or less.

The polyester (meth)acrylate oligomer, when used in a secondary coating composition, preferably has a Mn of at least about 500, more preferably, at least about 750, even more preferred, at least about 1,000. Preferably, its Mn is about 5,000 or less, more preferably, about 4,000 or less, even more preferred, about 2,500 or less, and most preferred, about 2,000 or less.

The polyester (meth)acrylate oligomer, when used in a matrix composition, preferably has a Mn of at least about 500, more preferably, at least about 1,000, even more preferred, at least about 1,500. Preferably, its Mn is about 15,000 or less, more preferably, about 10,000 or less, even more preferred, about 5,000 or less, and most preferred, about 3,000 or less.

The Mn of the polyester polyol generally lies between about 400 and about 14,500, preferably, between about 500 and about 10,000, more preferably, between about 600 and about 9,000.

With a view of obtaining the appropriate mechanical properties, the polyester (meth)acrylate used in the primary coating composition is preferably aliphatic, whereas the polyester (meth)acrylate used in the secondary coating or ink composition is preferably cycloaliphatic or aromatic, more preferred, aromatic. The polyester (meth)acrylate used in the matrix material preferably is aliphatic, cycloaliphatic or aromatic.

The OH-functionality of the polyester backbone in general will be lower than about 5, more preferably lower than about 3. The functionality of the polyester backbone in general will be at least about 1.5, preferably, at least about 1.8. Preferably, the functionality is about 2 to about 2.5. Similar ranges apply to the (meth)acrylate-functionality of the polyester (meth)acrylate of the present invention.

The polyester (meth)acrylate used in the coating compositions having a modulus of less than about 5 MPa (further called soft coating compositions), such as a primary coating composition preferably has a low functionality, preferably, between about 1.5 and 3, more preferably, between about 1.7 and 2.2 and most preferred, between about 2.0 and 2.2, whereas the polyester (meth)acrylate used in the coating compositions having a modulus of at least about 5 MPa (further called hard coating compositions), such as a secondary coating, an ink or a matrix composition, preferably has a higher functionality, preferably, between about 2 and 5, more preferred, between about 2.5 and 4, and most preferred between about 2.05 and about 3.5.

An alternative preferred option for use in secondary, ink and matrix compositions is using relatively higher Mw polyester (meth)acrylate oligomers with lower acrylate functionality, optionally together with higher Mw alkoxylated (pref. Ethoxylated) multifunctional monomer diluents. These result in secondary, ink and matrix compositions having a good balance between mechanical properties, cure speed and hydrolytic stability.

The radiation-curable primary coating composition according to the present invention generally comprises at least about 10 wt. % of the oligomer (A), preferably, at least about 20 wt. %, more preferably, at least about 30 wt. %, particularly preferred, at least about 50 wt. % and most preferred, at least about 70 wt. %. The primary coating composition generally comprises about 95 wt. % or less of the oligomer (A), preferably, about 90 wt. % or less, more preferably, about 87 wt. % or less, particularly preferred, about 85 wt. % or less. The weight % is taken to be relative to the total amount of the coating composition.

The primary coating composition of the present invention generally comprises about 90 wt. % or less of a reactive diluent (B), preferably, about 80 wt. % or less, more preferably, about 70 wt. % or less, particularly preferred, about 50 wt. % or less and most preferred, about 30 wt. % or less. The primary coating composition generally comprises at least about 5 wt. % of a reactive diluent (B), preferably, at least about 10 wt. %, more preferably, at least about 13 wt. %, particularly preferred, at least about 15 wt. %.

The primary coating composition of the present invention generally comprises between about 0.1 and about 20 wt. % of a photoinitiator (C), preferably, between about 0.2 and about 15 wt. %, more preferably, between about 0.3 and about 10 wt. %, particularly preferred, between about 0.5 and about 8 wt. %.

The radiation-curable secondary coating composition according to the present invention generally comprises at least about 10 wt. % of the oligomer (A), preferably, at least about 20 wt. %, more preferably, at least about 25 wt. %, particularly preferred, at least about 30 wt. % and most preferred, at least about 35 wt. %. The secondary coating composition generally comprises about 90 wt. % or less of the oligomer (A), preferably, about 85 wt. % or less, more preferably, about 80 wt. % or less, particularly preferred, about 60 wt. % or less, most preferred, about 50 wt. % or less.

The total weight percent of the components of the radiation curable coating composition of the present invention adds up to 100%.

The secondary coating composition of the present invention generally comprises a reactive diluent (B) and a photoinitiator (C) in the same amount ranges as given above for the primary coating composition.

The same amount ranges of the oligomer (A), reactive diluent (B), and photoinitiator (C) as given for the secondary coating composition above are typical for the ink and matrix composition of the present invention.

According to a preferred embodiment of the present invention, the radiation curable composition of the present invention, and in particular, the secondary coating and the matrix composition comprise a blend of an epoxy (meth) acrylate and a polyester (meth)acrylate oligomer (A).

Other oligomers can be present in addition to the polyester (meth)acrylate. Said other oligomer can be a urethane (meth)acrylate oligomer, comprising a (meth)acrylate group, urethane groups and a backbone.

Examples of suitable polyols to be used as backbones in the additional oligomer are polyether polyols, polyester polyols, polycarbonate polyols, polycaprolactone polyols, acrylic polyols, and the like. These polyols may be used either individually or in combinations of two or more. There are no specific limitations to the manner of polymerization of the structural units in these polyols. Any of random polymerization, block polymerization, or graft polymerization is acceptable. Examples of suitable polyols, polyisocyanates and hydroxylgroup-containing (meth)acrylates are disclosed in WO 00/18696, which is incorporated herein by reference.

The reduced number average molecular weight derived from the hydroxyl number of these polyols is usually from about 50 to about 25,000, preferably from about 500 to about 15,000, and more preferably from about 1,000 to about 8,000.

Preferably, the primary coating composition of the present invention comprises less than about 40 wt. % of a urethane (meth)acrylate oligomer, more preferred, less than about 35 wt. %, particularly preferred, less than about 30 wt. %, and most preferred, less than about 25 wt. %. The amount of urethane (meth)acrylate oligomer preferably is low, more preferred, there is substantially no urethane (meth)acrylate oligomer present. The urethane (meth)acrylate oligomer, if present, preferably, is polyether-based urethane (meth) acrylate oligomer, more preferred, an aliphatic polyether urethane (meth)acrylate oligomer.

The radiation-curable secondary coating composition according to the present invention preferably comprises an epoxy (meth)acrylate or urethane (meth)acrylate in addition to the polyester (meth)acrylate (A). The epoxy (meth) acrylate preferably is present in an amount between about 10 and about 90 wt. %, more preferably, between about 30 and 60 wt. %, particularly preferred, between 35 and about 50 wt. %. If no epoxy (meth)acrylate is present, the amount of the polyester (meth)acrylate oligomer (A) preferably is between about 70 and 90 wt. %. If a urethane (meth)acrylate oligomer is present, it is preferably present in the same amount ranges as given above for the primary coating composition, The reactive diluent (B) is preferably added in such an amount that the viscosity of the coating composition at room temperature is in the range of about 500 to about 20,000 mPa·s, preferably in the range of about 1,000 to about 10,000 mPa·s, more preferably, in the range of about 1,500 to about 5,000 mPa·s.

A reactive diluent preferably has a molecular weight of not more than about 550 or a viscosity at room temperature of not more than about 300 mPa·s (measured as 100% diluent). However, alkoxylated bisphenol A type compounds, such as ethoxylated bisphenol A, which can be regarded as a reactive diluent, have viscosities of not more than about 2000 mPa·s.

As the reactive diluent (B), a polymerizable monomer containing a vinyl group or a (meth)acryloyl group can be added to the liquid curable resin composition of the present invention. Monofunctional monomers and polyfunctional monomers are included in such polymerizable monomers.

Examples of suitable monofunctional monomers include monomers containing a vinyl group, such as N-vinyl pyrrolidone, N-vinyl caprolactam, vinyl imidazole, vinyl pyridine; isobornyl (meth)acrylate, bornyl (meth)acrylate, tricyclodecanyl (meth)acrylate, dicyclopentanyl (meth) acrylate, dicyclopentenyl (meth)acrylate, cyclohexyl (meth) acrylate, benzyl (meth)acrylate, 4-butylcyclohexyl (meth) acrylate, acryloyl morpholine, 2-hydroxyethyl (meth) acrylate, 2-hydroxypropyl (meth)acrylate, 2-hydroxybutyl (meth)acrylate, methyl (meth)acrylate, ethyl (meth)acrylate, propyl (meth)acrylate, isopropyl (meth)acrylate, butyl (meth)acrylate, amyl (meth)acrylate, isobutyl (meth) acrylate, t-butyl (meth)acrylate, pentyl (meth)acrylate, caprolactone acrylate, isoamyl (meth)acrylate, hexyl (meth) acrylate, heptyl (meth)acrylate, octyl (meth)acrylate, isooctyl (meth)acrylate, 2-ethylhexyl (meth)acrylate, nonyl (meth)acrylate, decyl (meth)acrylate, isodecyl (meth) acrylate, undecyl (meth)acrylate, dodecyl (meth)acrylate, lauryl (meth)acrylate, stearyl (meth)acrylate, isostearyl (meth)acrylate, tetrahydrofurfuryl (meth)acrylate, butoxyethyl (meth)acrylate, ethoxydiethylene glycol (meth) acrylate, benzyl (meth)acrylate, phenoxyethyl (meth) acrylate, polyethylene glycol mono(meth)acrylate, polypropylene glycol mono(meth)acrylate, methoxyethylene glycol (meth)acrylate, ethoxyethyl (meth)acrylate, methoxypolyethylene glycol (meth)acrylate, methoxypolypropylene glycol (meth)acrylate, diacetone (meth) acrylamide, isobutoxymethyl (meth)acrylamide, N,N-dimethyl (meth)acrylamide, t-octyl (meth)acrylamide, dimethylaminoethyl (meth)acrylate, diethylaminoethyl (meth)acrylate, 7-amino-3,7-dimethyloctyl (meth)acrylate, N, N-diethyl (meth)acrylamide, N,N-dimethylaminopropyl (meth)acrylamide, hydroxybutyl vinyl ether, lauryl vinyl ether, cetyl vinyl ether, 2-ethylhexyl vinyl ether; and compounds represented by the following formula (6)

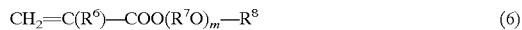

$$CH_2=C(R^6)-COO(R^7O)_m-R^8 \qquad (6)$$

wherein $R^6$ is a hydrogen atom or a methyl group; $R^7$ is an alkylene group containing 2 to 8, preferably 2 to 5 carbon atoms; and m is an integer from 0 to 12, and preferably from 1 to 8; $R^8$ is a hydrogen atom or an alkyl group containing 1 to 12, preferably 1 to 9, carbon atoms; or, $R^8$ is a tetrahydrofuran group—comprising alkyl group with 4–20 carbon atoms, optionally substituted with alkyl groups with 1–2 carbon atoms; or $R^8$ is a dioxane group-comprising alkyl group with 4–20 carbon atoms, optionally substituted with methyl groups; or $R^8$ is an aromatic group, optionally substituted with $C_1$–$C_{12}$ alkyl group, preferably a $C_8$–$C_9$ alkyl group, and alkoxylated aliphatic monofunctional monomers, such as ethoxylated isodecyl (meth)acrylate, ethoxylated lauryl (meth)acrylate, and the like. Commercially available monofunctional compounds include ARONIX M111, M113, M114, M117 (Toagosei Chemical Industry Co., Ltd.), KAYARAD TC110S, R629, R644 (Nippon Kayaku Co., Ltd.), and VISCOAT 3700 (Osaka Organic Chemical Industry, Ltd.).

Examples of the polyfunctional monomers include monomers containing (meth)acryloyl group such as trimethylolpropane tri(meth)acrylate, pentaerythritol (meth)acrylate, ethylene glycol di(meth)acrylate, tetraethylene glycol di(meth)acrylate, polyethylene glycol di(meth)acrylate, 1,4-butanediol di(meth)acrylate, 1,6-hexanediol di(meth) acrylate, neopentyl glycol di(meth)acrylate, trimethylolpropanetrioxyethyl (meth)acrylate, tris(2-hydroxyethyl) isocyanurate tri(meth)acrylate, tris(2-hydroxyethyl) isocyanurate di(meth)acrylate, tricyclodecane diyl dimethyl di(meth)acrylate, and di(meth)acrylate of a diol which is an ethylene oxide or propylene oxide adduct to bisphenol A, di(meth)acrylate of a diol which is an ethylene oxide or propylene oxide adduct to hydrogenated bisphenol A, epoxy (meth)acrylate which is a (meth)acrylate adduct to bisphenol A of diglycidyl ether, diacrylate of polyoxyalkylated bisphenol A, and triethylene glycol divinyl ether, adduct of hydroxyethyl acrylate, isophorone diisocyanate and hydroxyethyl acrylate (HIH), adduct of hydroxyethyl acrylate, toluene diisocyanate and hydroxyethyl acrylate (HTH), and amide ester acrylate. Given as commercially available polyfunctional monomers are YUPIMER-SA1002, YUPIMER-SA2007 (Mitsubishi Chemical Co., Ltd.), VISCOAT 700 (Osaka Organic Chemical Industry Ltd.), KAYARAD R-604, DPCA-20, DPCA-30, DPCA-60, DPCA-120, HX-620, D-310, D-330, (Nippon Kayaku Co., Ltd.), SR-349 (Sartomer) and ARONIX M-210, M-215, M-315, M-325 (Toagosei Chemical Industry Co., Ltd.). Among these polyfunctional monomers, tricyclodecane dimethyl di(meth)acrylate and diacrylate of polyoxyalkylated bisphenol A are preferred.

Particularly preferred reactive diluents in the radiation curable coating compositions of the present invention are ethoxylated nonyl phenol acrylate and propoxylated nonyl phenol acrylate. These diluents have shown to have a positive effect on the hydrolytic resistance of the coating composition. Moreover, ethoxylated nonyl phenolacrylate helps to achieve the required mechanical properties of the primary coating, in particular its low Tg and also of the secondary coating, in particular, its elongation.

Further, reactive diluents are preferred that—besides the (meth)acrylate functionalities—do not contain additional ester groups.

For the primary coating compositions of the present invention, caprolactone acrylate, ethoxylated (n=4) lauryl acrylate or mixtures thereof are preferred as reactive diluents (B), in particular to optimize the viscosity and Tg. These preferred reactive diluents also contribute to the good hydrolytic stability of the radiation-curable composition of the present invention.

Preferred reactive diluents (B) for the secondary coating composition of the present invention are propoxylated trimethylol propane triacrylate (PTMPTA), propoxylated neopentyl glycol diacrylate (PNPGDA), ethoxylated hexane diol diacrylate (EHDDA), propoxylated hexane diol diacrylate (PHDDA), propoxylated glycerol triacrylate (GPTA) or mixtures thereof. The use of these reactive diluents in the secondary coating composition results in a relatively high cure speed and modulus.

Preferred reactive diluents (B) for the matrix material of the present invention are the ones described above as being preferred for the secondary coating, and isobornyl acrylate (IBOA), hexane diol diacrylate (HDDA), phenoxy ethyl acrylate (PEA) or mixtures thereof. Particularly preferred for the matrix material of the present invention is a mixture of substantially equal amounts of IBOA, HDDA and PEA.

Preferred reactive diluents (B) for the ink composition of the present invention are pentaerithritol tetra acrylate (PETA), IBOA, HDDA, PEA, or alkoxylated derivatives thereof, or mixtures thereof.

The liquid curable resin composition of the present invention can be cured by radiation. As used in this application, the term radiation means radiation such as visible light, ultraviolet light or electron beam. A photoinitiator (C) can also be added to the liquid curable resin composition of the present invention.

Preferably, the photoinitiators (C) are free radical photoinitiators.

Free-radical photoinitiators are generally divided into two classes according to the process by which the initiating radicals are formed. Compounds that undergo unimolecular bond cleavage upon irradiation are termed Type I or homolytic photoinitiators. If the excited state photoinitiator interacts with a second molecule (a coinitiator) to generate radicals in a bimolecular reaction, the initiating system is termed a Type II photoinitiator. In general, the two main reaction pathways for Type II photoinitiators are hydrogen abstraction by the excited initiator or photoinduced electron transfer, followed by fragmentation.

Examples of suitable free-radical photoinitiators are disclosed in WO 00/18696 and are incorporated herein by reference.

Preferably, the total amount of photoinitiators present is between about 0.10 wt. % and about 20.0 wt. % relative to the total amount of the coating composition. More preferably, the total amount is at least about 0.5 wt. %, particularly preferred, at least about 1.0 wt. %, and most preferred, at least about 2.0 wt. %. Moreover, the total amount is preferably less than about 15.0 wt. %, more preferably, less than about 10.0 wt. %, and particularly preferred, less than about 6.0 wt. % In one preferred embodiment of the present invention at least one of the photoinitiators contains a phosphorous, sulfur or nitrogen atom. It is even more preferred that the photoinitiator package comprises at least a combination of a photoinitiator containing a phosphorous atom and a photoinitiator containing a sulfur atom.

In another preferred embodiment of the invention, at least one of the compounds (C) is an oligomeric or polymeric photoinitiator.

The radiation curable coating composition of the present invention preferably contains one or two phosphine oxide type photoinitiators, such as TPO-type or bisacyl phosphine oxide type (BAPO) photoinitiators, and/or a-hydroxyketo-type photoinitiator (Irgacure 184 or Darocur 1173). Even more preferred is a mixture of BAPO, Lucirin TPO, Irgacure 184, Darocur 1173, and Irgacure 907. If Irgacure 907 (2-methyl-1-[4-(methylthio)phenyl]-2-morpholino propan-1-one, available from Ciba-Geigy) is present in a low amount, said combination of photoinitiators shows remarkably high cure speed and acceptably low yellowing.

As an additive (D), an amine compound can be added to the liquid curable resin composition of the present invention to prevent generation of hydrogen gas, which causes transmission loss in the optical fibers. As examples of the amine that can be used herein, diallylamine, diisopropylamine, diethylamine, diethylhexylamine, and the like can be given.

In addition to the above-described components, various additives such as antioxidants, UV absorbers, light stabilizers, silane coupling agents, coating surface improvers, heat polymerization inhibitors, leveling agents, surfactants, colorants, preservatives, plasticizers, lubricants, solvents, fillers, aging preventives, and wettability improvers can be used in the liquid curable resin composition of the present invention, as required.

The description can also apply to colored primary coating, colored secondary coating, ink and colored matrix compositions. The colorant can be a pigment or dye, preferably, a dye, more preferably a reactive dye.

The viscosity of the liquid curable resin composition of the present invention at 23° C. is usually in the range from about 200 to about 20,000 cP, and preferably from about 2,000 to about 15,000 cP.

In general, optical fibers are coated first with a primary coating and subsequently with a secondary coating. The coatings can be applied as a wet-on-wet system (without first curing of the primary) or as a wet-on-dry system. The primary coating can be colored with a dye, or secondary coatings can be colored with pigments or dyes, or a clear secondary can be further coated with an ink. The primary and secondary coatings generally have a thickness of about 30 µm each. An ink coating generally has a thickness of about 5 µm (3–10 µm). An ink generally is colored with pigments.

The coated and preferably colored optical fibers can be used in a ribbon comprising a plurality of said optical fibers, generally in a parallel arrangement. The plurality of optical fibers is further coated with one or more matrix materials in order to obtain a ribbon.

The invention will be further elucidated by the following examples and test methods.

EXAMPLES AND COMPARATIVE EXPERIMENTS

Synthesis of polyester acrylates I–IV:

The polyester acrylates I–IV are prepared according to the 2-step synthesis process as described above. In step 1, isophthalic acid (IPA) is reacted with 2-butyl-2-ethyl-1,3-propanediol (BEPD) in the presence of 0.2% (based on total amount of IPA and BEPD) of BuSnOOH as a catalyst. The end of step 1 is indicated when the acid value (AV) is below 5 and all IPA is dissolved.

The general experimental conditions of step 2 are:

| | |
|---|---|
| amount acrylic acid (AA): | 105 mol % (to OH) |
| amount toluene: | 35 wt. % (based on total amount of IPA + BEPD + AA) |
| amount PTSA: | 1 wt. % (based on IPA + BEPD + AA) |
| inhibition system: | 1000 ppm DBH, 1000 ppm TNPP, air purge (1 l/h/l) |
| reaction temperature: | 125–130° C. |
| reaction time: | 12–16 hours (till > 95% OH conversion by NMR) |
| PTSA neutralisation: | reaction with 150 mol % of neutralizer |
| solvent distillation: | at 120° C. and 20 mbar (till the amount of toluene left is less than about 0.5%) |

The amounts of the reactants used in said process are given for each of the polyester acrylates I–IV:

Polyester acrylate I: 5 mol BEPD, 4 mol IPA and 2 mol AA, neutralized with 3-ethyl-3-hydroxymethyl-oxetane (UVR-6000), theoretical Mn=1428

Polyester acrylate II: 5 mol BEPD, 4 mol IPA and 2 mol AA, neutralized with trimethyl ortho formate, theoretical Mn=1428

Polyester acrylate III: 3.5 mol BEPD, 2.5 mol IPA and 2 mol AA, neutralized with 3-ethyl-3-hydroxymethyl-oxetane (UVR-6000), theoretical Mn=1020

Polyester acrylate IV: 6.5 mol BEPD, 5.5 mol IPA and 2 mol AA, neutralized with 3-ethyl-3-hydroxymethyl-oxetane (UVR-6000), theoretical Mn=1880.

The neutralization was completed till the acid value of strong acid is substantially equal to zero.

Synthesis of Alkyd Acrylate V:

The alkyd acrylate V is prepared according to a 3-step synthesis process. In the first step, 1 mol coconut fatty acid (Prifac7901 of Unichema) was reacted with 1 mol trimethylol propane (TMP) with BuSnOOH at 185° C. till the acid value is below 5. In the second step, the fatty acid diol was reacted with 3 mol neopentyl glycol (NPG), 2 mol IPA and 1 mol adipic acid (ADA) till the acid value was below 5 to make an alkyd polyol. In the last step, this polyol was acrylated with acrylic acid in refluxing toluene (130° C.) with 1% PTSA as catalyst. The OH conversion was followed by NMR. After about 95% conversion, the PTSA was neutralised with cyclohexene oxide and the solvent was evaporated. Finally a yellow viscous resin was obtained (GPC Mn/Mw=1600/4800).

Synthesis of Polyester Acrylate VI:

The polyester acrylate VI is prepared according to a 2-steps process as follows: In step 1, 2 mol isophthalic acid and 3 mol Pripol 2033 (a C36 reduced dimer acid diol of Uniqema) were esterified with 1% PTSA as a catalyst at 160–180° C. and 4% toluene in a flask equipped with a Dean-Stark set up to remove the reaction water. After 3 hours the AV was 3.

In step 2, the polyester polyol was cooled down to 100° C. and mixed with 105 mol % acrylic acid (to amount OH), 15% toluene and 0.1% dibutylhydroquinon DBH (all based on amount polyester polyol+acrylic acid). Air was purged through the reaction mixture and the temperature was increased till boiling toluene. Next, the mixture was refluxed at a temperature between 120–130° C. for 4 hours. If necessary, the pressure was reduced to keep the toluene refluxing. After 4 hours a sample was taken and titrated, the AV of the strong acid was 1.3.

Next, the resin was neutralised with 150 mol % (to AV of the strong acid) of 3-methyl-3-hydroxymethyl-oxetane. After 15 min a sample was taken to check if the AV of the strong acid was equal to 0 and subsequently the solvent and residual acrylic acid were removed via a distillation at 130° C. and 50 mm Hg. (functionality of 2.0).

Example 1 (Primary Coatings) and Comparative Experiment A (Single Coating)

TABLE 1

| | Ex. 1 (wt. %) | Ex. 2 (wt. %) | Compar. Exp. A (wt. %) |
|---|---|---|---|
| Polyester acrylate IV | 74.5 | | |
| Polyester acrylate VI | | 84.2 | |
| Polyester acrylate A | | | 76.2 |
| CD-9075 | 20.0 | 10.0 | |
| Neopentyl glycol diacrylate | | | 19.0 |
| Benzoin isopropyl ether | | | 4.8 |
| Chivacure TPO | 0.5 | 0.5 | |
| Chivacure 184 | 2.0 | 2.0 | |
| Chivacure 173 | 2.0 | 2.0 | |
| A-189 | 1.0 | 1.0 | |
| Tensile strength (MPa) | 0.5 | 0.8 | 30 |
| Elongation (%) | 61 | 40 | 13 |
| Modulus (MPa) | 1.3 | 3.3 | 930 |
| Tan delta max (° C.) | 3 | −33 | 43 |
| TGA weight loss (%) | 6.1 | | 13.8 |
| OIT (° C.) | 242 | | 215 |
| cure speed (J/cm2) | | | 1.8 |
| FTIR cure (%) | 34.6 | 11 | |
| 85° C./85% RH, $E_o$-change (%): | | | |
| after 10 days | −4.5 | | Too fragile |
| after 30 days | −27.3 | | Too fragile |

Polyester acrylate A is derived from phthalic anhydride, ethylene glycol and acrylic acid (synthesis see below) as described in Ex.2 (referring back to Ex.1) of JP-5792552 of Nitto Electric Ind.
CD-9075 = ethoxylated (n = 4) lauryl acrylate
Chivacure TPO is 2,4,6-trimethylbenzoyl diphenyl phosphine oxide, available from Chitec Chemical Company, Ltd.
Chivacure 184 is 1-hydroxy-cyclohexyl-phenyl ketone, available from Chitec Chemical Compamy, Ltd.
Chivacure 173 is 2-hydroxy-2-methyl-1-phenylpropan-1-one, available from Chitec Chemical Compamy, Ltd.
A-189 is 1-propanethiol-3-(trimethoxysilyl)
FTIR cure % is obtained by the ratio of the % RAU after 0.2 sec exposure to the % RAU after 10 sec exposure: (0.2 sec RAU/10 sec RAU) × 100

The polyester acrylate A of Comparative Experiment A (which is Ex.2 of JP-5792552 of Nitto Electric Ind.) is prepared as follows:

A linear polyester polyol was made by reaction of 4 mol phthalic anhydride and 5 mol ethylene glycol with 1% p-toluene sulfonic acid (PTSA) as catalyst at 130° C. Toluene was added to enhance the water removal (Dean Stark set-up). When the acid value (AV) was <10 mg KOH/g resin, 2 mol acrylic acid, 1000 ppm 2,5-dibutylhydroquinone and again 1% PTSA were added. After the acrylation the solvent was removed at 130° C. and 40 mbar. Then, the resin was diluted with neopentylglycol diacrylate (80 parts resin: 20 parts NPGDA).

From the results in Table 1 it is clear that the primary coating of Ex.1 containing a polyester acrylate oligomer according to the present invention has improved stability, more in particular, the coating is sufficiently hydrolytically stable to maintain mechanical integrity for at least 10 days under the 85° C./85% RH-test conditions and even remains intact after 30 days aging under these conditions. Its change in equilibrium modulus $E_o$ after aging under the above conditions is 4.5% after 10 days and 27%% after 30 days which shows that this coating is very stable. Moreover, acceptable mechanical properties are achieved for the primary coatings of the present invention, in particular the modulus of the coatings of Ex. 1 and 2 are appropriate for use as a primary coating. This is in contrast with the modulus of the Comparative Experiment A, which is unacceptably high for a primary or single coating by current requirements. Further, the coating of Ex. 2 shows an even more appropriate Tg for being used as a primary coating. Moreover, the coating of Ex. 2 is hydrolytically stable under the required conditions.

On the contrary, the single coating of Comparative Experiment A showed insufficient hydrolytic stability since the coating after being aged for 10 days under the above conditions was too fragile to be tested and actually, it fell apart during preparation of a sample thereof and/or during testing.

Moreover, the TGA weight loss of the coatings of the present invention was much lower and the OIT was higher than the coating of Comparative Experiment A, indicating its greater oxidative stability.

Examples 3–6 (Secondary Coatings)

TABLE 2

|  | Ex. 3 (wt. %) | Ex. 4 (wt. %) | Ex. 5 (wt. %) | Ex. 6 (wt. %) |
|---|---|---|---|---|
| CN120Z | 35.0 | 35.0 | 35.0 | 35.0 |
| Polyester acrylate VII | 40.0 |  |  |  |
| Polyester acrylate VIII | 40.0 |  |  |  |
| Polyester acrylate I |  |  | 40.0 |  |
| Polyester acrylate III |  |  |  | 40.0 |
| SR-504 | 22.0 | 22.0 | 22.0 | 22.0 |
| Chivacure TPO | 0.7 | 0.7 | 0.7 | 0.7 |
| Irgacure 819 | 0.3 | 0.3 | 0.3 | 0.3 |
| Chivacure 184 | 1.0 | 1.0 | 1.0 | 1.0 |
| Chivacure 173 | 1.0 | 1.0 | 1.0 | 1.0 |
| Tensile strength (MPa) | 33 | 29 | 23 | 22 |
| Elongation (%) | 4 | 4 | 10 | 10 |
| Modulus (MPa) | 1030 | 920 | 680 | 600 |
| Tan delta max (° C.) | 59 | 59 | 43 | 43 |
| TGA weight loss(%) | 4.1 | 5.2 | 4.3 | 4.5 |
| OIT(° C.) | 234 | 212 | 236 | 228 |
| FTIR cure (%) | 49.8 | 67.3 | 36.7 | 28.7 |

TABLE 2-continued

|  | Ex. 3 (wt. %) | Ex. 4 (wt. %) | Ex. 5 (wt. %) | Ex. 6 (wt. %) |
|---|---|---|---|---|
| 85° C./85% RH, $E_o$-change (%) |  |  |  |  |
| 10 days | −0.4 | −8.1 | −9.9 | −4 |
| 30 days | −3.5 | −22.6 | −24.9 | −2.5 |

CN120Z is bisphenyl A epoxy diacrylate from Sartomer
Polyester acrylate VII is CN-292, supplied by Sartomer
Polyester acrylate VIII is LR-8800, supplied by BASF, is derived from phthalic acid, trimethylol propane, ethoxylated bisphenol A and acrylic acid, and has a Mn of 900, a functionality of 3.5 and an acid value of maximum 5
SR-504 is ethoxylated nonyl phenyl acrylate from Sartomer
Chivacure TPO is 2,4,6-trimethylbenzoyl diphenyl phosphine oxide, available from Chitec Chemical Company, Ltd.
Irgacure 819 is bis (2,4,6-trimethylbenzoyl)-phenyl-phosphine-oxide, available from Ciba-Geigy
Chivacure 184 is 1-hydroxy-cyclohexyl-phenyl ketone, available from Chitec Chemical Compamy, Ltd.
Chivacure 173 is 2-hydroxy-2-methyl-1-phenylpropan-1-one, available from Chitec Chemical Compamy, Ltd.

From the results in Table 2 it is clear that the secondary coatings containing a polyester acrylate oligomer according to the present invention show good stability, in particular good hydrolytic stability, low TGA weight loss (good thermal stability) and sufficiently high OIT (good oxidative stability).

Moreover, acceptable tensile, elongation, modulus, and Tg could be obtained for these secondary coatings.

Examples 7–10(Matrix Materials) and Comparative Experiment B (Matrix Material)

TABLE 3

|  | Ex. 7 (wt. %) | Ex. 8 (wt. %) | Ex. 9 (wt. %) | Ex. 10 (wt. %) | Comp. Exp. B (wt. %) |
|---|---|---|---|---|---|
| PTMG650-TDI-HEA |  | 39.57 |  |  |  |
| Polyester acrylate IX | 74.5 |  |  |  |  |
| CN120Z |  |  | 29.43 |  |  |
| Polyester acrylate III |  | 29.43 |  |  |  |
| Polyester acrylate I |  |  | 39.57 | 62.8 |  |
| Polyester acrylate B |  |  |  |  | 48.5 |
| SR-495 | 20.0 |  |  |  |  |
| Isobornyl acrylate |  | 10.14 | 10.14 | 24.3 |  |
| Hexane diol diacrylate |  | 6.92 | 6.92 | 9.7 |  |
| Phenoxy ethyl acrylate |  | 9.89 | 9.89 | 0.3 |  |
| Genomer 1122 |  |  |  |  | 48.5 |
| Lucirin TPO | 0.5 | 2.03 | 2.03 |  |  |
| Chivacure 184 | 2.0 |  |  |  |  |
| Darocur 1173 | 2.0 |  |  | 2.9 | 3.0 |
| Tinuvin 292 |  | 0.50 | 0.50 |  |  |
| Irganox 245 |  | 0.50 | 0.50 |  |  |
| A-189 | 1.0 |  |  |  |  |
| DC 190 |  | 0.66 | 0.66 |  |  |
| DC 57 |  | 0.36 | 0.36 |  |  |
| Tensile strength (Mpa) | 2.4 | 18 | 50 | 38 | 0.6 |
| Elongation (%) | 12 | 61 | 4 | 7 | 22 |
| Modulus (MPa) | 21.8 | 120 | 1600 | 1220 | 3.4 |
| Tan delta max (° C.) | 21 | 36 | 63 | 49 | −6 |
| TGA weight loss (%) | 6.2 | 2.3 | 2.6 |  | 22.6 |
| OIT (°0 C.) | 221 | 230 | 165 |  | 214 |
| FTIR cure (%) | 57.9 | 57.4 | 59.7 |  | 18.1 |
| 85° C./85% RH, |  |  |  |  |  |

TABLE 3-continued

| | Ex. 7 (wt. %) | Ex. 8 (wt. %) | Ex. 9 (wt. %) | Ex. 10 (wt. %) | Comp. Exp. B (wt. %) |
|---|---|---|---|---|---|
| $E_o$-change (%) | | | | | |
| 10 days | −19.9 | 0 | 18.9 | −2.8 | too fragile |
| 30 days | −56.5 | 0.8 | −22.9 | −11.9 | too fragile |

PTMG650-TDI-HEA is a polyether based urethane acrylate oligomer

Polyester acrylate IX is PE-55F, supplied by BASF, derived from adipic acid, phthalic acid, trimethylol propane, ethtlene glycol or TTEG and acrylic acid, having Mn of 1000, functionality 2.5, and acid value of maximum 5

Polyester acrylate B is derived from adipic acid/neopentyl glycol/acrylic acid as described below (described as reaction product 2 in DE-A1-4126860 of Bayer)

SR-495 is caprolactone acrylate

Genomer 1122 is 2-(N-butylcarbamoyl) ethyl acrylate, supplied by Rahn

Lucirin TPO is 2,4,6-trimethylbenzoyl diphenyl phosphine oxide, available from BASF Darocur 1173 is 2-hydroxy-2-methyl-1-phenylpropane-1-one, available from Ciba-Geigy Tinuvin 292 is bis(1,2,2,6,6-pentamethyl-4-piperidinyl) sebacate from Ciba Irganox 245 is ethylene bis(oxyethylene) bis(3-tert-butyl-4-hydroxy-5-methylhydrocinnamate) from Ciba DC190 is (dimethylsiloxane)-(polyoxypropylene/polyoxyethylene glycol acetate) copolymer from Dow Corning DC57 is a polysiloxane from Dow Corning The Polyester acrylate B of Comparative Experiment B (which is composition 1 as described in DE-A1-4126860 of Bayer) was prepared as follows:

A linear polyester polyol was made by reaction of 4 mol adipic acid and 5 mol neopentyl glycol with 0.1% BuSnCI (OH)$_2$ as catalyst at 180° C. Some toluene was added to enhance the water removal (Dean Stark set-up). When the acid value was 1 mg KOH/g resin, the temperature was decreased to 130° C. and 2 mol acrylic acid, 1000 ppm 2,5-dibutylhydroquinone, 1% PTSA and 15% toluene were added. After the acrylation reaction the solvent was removed at 130° C. and 40 mbar.

From the results in Table 3 it is clear that matrix materials containing a polyester acrylate oligomer according to the present invention having acceptable tensile, elongation, modulus, and Tg could be formulated. These matrix materials show very good hydrolytic stability and low TGA weight loss compared to the Comparative Experiment B. The film of the comparative matrix material B, after being aged for 10 days under the above aging conditions, was too fragile to be measured and simply fell apart during preparation of the sample and/or during testing thereof.

TABLE 4

| | Ex.11 (wt. %) | Ex. 12 (wt. %) | Ex. 13 (wt. %) | Ex. 14 (wt. %) | Ex. 15 (wt. %) | Ex. 16 (wt %) | Ex. 17 (wt %) | Ex. 18 (wt %) | Ex. 19 (wt %) |
|---|---|---|---|---|---|---|---|---|---|
| CN120Z | 33.0 | 33.0 | 33.0 | 33.0 | 40.0 | 40.0 | 35.0 | 33.0 | 40.0 |
| Polyester acrylate VIII | | | | | | | 39.7 | | |
| Polyester acrylate IX | | | | | | | | 31.7 | |
| Polyester acrylate X | 31.7 | | | | | | | | |
| Polyester acrylate XI | | 31.7 | | | | | | | |
| Polyester acrylate XII | | | 31.7 | | | | | | |
| Polyester acrylate XIII | | | | 31.7 | | | | | |
| Polyester acrylate XIV | | | | | 25.0 | | | | |
| Polyester acrylate XV | | | | | | 25.0 | | | |
| Polyester acrylate XVI | | | | | | | | | 25.0 |
| SR-502 | 22.0 | 22.0 | 22.0 | 22.0 | 10.0 | 10.0 | | 22.0 | 10.0 |
| SR-504D | | | | | | | | | 16.7 |
| Photomer 4039 | 10.0 | 10.0 | 10.0 | 10.0 | 5.0 | 5.0 | 22.0 | 10.0 | 5.0 |
| Chivacure 184 | 1.0 | 1.0 | 1.0 | 1.0 | 1.0 | 1.0 | 1.0 | 1.0 | 1.0 |
| Darocur 1173 | 1.0 | 1.0 | 1.0 | 1.0 | 1.0 | 1.0 | 1.0 | 1.0 | 1.0 |
| Chivacure TPO | 0.7 | 0.7 | 0.7 | 0.7 | 0.7 | 0.7 | 0.7 | 0.7 | 0.7 |
| Irgacure 819 | 0.3 | 0.3 | 0.3 | 0.3 | 0.3 | 0.3 | 0.3 | 0.3 | 0.3 |
| Irganox 1035 | 0.3 | 0.3 | 0.3 | 0.3 | 0.3 | 0.3 | 0.3 | 0.3 | 0.3 |
| Tensile strength (MPa) | 41 | 26 | 26 | 24 | 28 | 25 | 38 | 32 | 30 |
| Elongation (%) | 4 | 8 | 14 | 22 | 13 | 21 | 8 | 12 | 12 |
| Modulus (MPa) | 1340 | 770 | 590 | 390 | 800 | 540 | 1100 | 860 | 830 |
| TGA weight loss (%) | | | | | | | 5.1 | 3.8 | 4.2 |
| OIT (° C.) | | | | | | | 245 | 248 | 260 |
| 95% cure (J/cm$^2$) | | | | | | | 0.34 | 0.36 | 0.33 |
| Tan delta max (° C.) | 58 | 48 | 49 | 44 | 46 | 47 | 52 | 51 | 46 |
| FTIR cure (%) | 67.3 | 77.0 | 76.1 | 65.7 | 63.4 | 67.1 | 78.5 | 74.5 | 63.0 |
| 85° C./85% RH: | | | | | | | | | |
| $E_o$-change (%), 30 days | +2.2 | −22.9 | −8.8 | −24.6 | −16.6 | −9.8 | | | |
| 85° C./85% RH: | | | | | | | | | |
| Weight change (%), 60 d. | | | | | | | −0.6 | −0.0 | −1.0 |
| Δ tan delta max (° C.), 60 d. | | | | | | | +4 | −1 | +5 |

TABLE 4-continued

|  | Ex.11 (wt. %) | Ex. 12 (wt. %) | Ex. 13 (wt. %) | Ex. 14 (wt. %) | Ex. 15 (wt. %) | Ex. 16 (wt %) | Ex. 17 (wt %) | Ex. 18 (wt %) | Ex. 19 (wt %) |
|---|---|---|---|---|---|---|---|---|---|
| E-change (%), 60 days: | | | | | | | | | |
| 85° C./85% RH | | | | | | | -9.2 | -29.2 | -10.2 |
| 85° C./dry conditions | | | | | | | 11.8 | 0.2 | 14.2 |
| Low intensity fluorescence | | | | | | | 19.1 | 2.1 | 42.3 |

Polyester acrylate X is CN-2251, Sartomer analog of PE-55F from BASF
Polyester acrylate XI is Actilane 505, a tetrafunctional polyester acrylate supplied by Akzo Nobel
Polyester acrylate XII is Actilane 579, a trifunctional polyester acrylate supplied by Akzo Nobel
Polyester acrylate XIII is Stepanpol PS-2002, supplied by Stepan and derived from phthalic anhydride, diethylene glycol and acrylic acid, having a Mw of 670 and functionality of 2.0
Polyester acrylate XIV is prepared according to the 2-steps synthesis process as described for polyester acrylates I–IV and is derived from 2.5 mol isophthalic acid, 3.3. mol BEPD, 0.2 mol trimethylol propane and 2.2 mol acrylic acid, having Mw of 935 and acrylate functionality of 2.2 with 15% PEA, OH-conversion is 97%
Polyester acrylate XV is analogue to polyester acrylate XIIII, but having a OH-conversion of 90%
Polyester acrylate XVI is prepared according to the 2-steps synthesis process as described for polyester acrylates I–IV and is derived from isophthalic acid, BEPD, neopentyl glycol and acrylic acid, having Mw of 944 and functionality of 2.0
SR-502 is ethoxylated (n = 9) trimethylol propane triacrylate, supplied by Sartomer
Photomer 4039 is ethoxylated (n = 3) phenoxy ethyl acrylate The coatings of Examples 11–19 show acceptable mechanical properties to be useful as secondary coatings or as matrix materials, show improved FTIR cure speeds while maintaining good hydrolytic stability.

Example 20 (Ink Material)

TABLE 5

|  | Ex. 20 (wt. %) |
|---|---|
| CN120Z | 31.60 |
| Polyester acrylate III | 18.60 |
| PETA | 9.28 |
| Isobornyl acrylate | 2.85 |
| Hexane diol diacrylate | 10.14 |
| Phenoxy ethyl acrylate | 2.85 |
| Darocur 4265 | 10.14 |
| BHT | 0.51 |
| Ebecryl 350 | 2.03 |
| 9W135 white | 3.00 |
| 9S4 blue | 9.00 |
| Release from matrix | Pass |
| Adhesion to secondary | Good |
| RAU in inert atmosphere (%) | 82.0 |
| RAU in air (%) | 74.2 |

CN120Z is bisphenol A epoxy diacrylate from Sartomer
PETA is pentaerythritol tetraacrylate from Sartomer
Darocur 4265 is a 50/50 blend of Lucirin TPO and Darocur 1173 from Ciba The cured ink of example 20 (see test method) shows a good adhesion to the secondary coating (commercial UV-curable urethane acrylate based secondary coating, supplied by Desotech), and the matrix (commercial UV-curable urethane acrylate based matrix material, supplied by Desotech) showed a good break-out from the ink layers.

Description of Test Methods

Tensile Strength, Elongation and Modulus Test Method

The tensile properties of cured samples were tested using a universal testing instrument, Instron Model 4201 equipped with a suitable personal computer and Instron software to yield values of tensile strength, percent elongation at break, and secant or segment modulus. Load cells had 2 or 20 pound capacity, or metric equivalents.

To prepare the samples for testing, a drawdown (cured film) of each material to be tested was made on a glass plate and cured using a UV processor. The cured film was conditioned at 23±2° C. and 50±5% relative humidity for a minimum of sixteen hours prior to testing. A minimum of eight test specimens, having a width of 0.5±0.002 inches and a length of 5 inches, were cut from the cured film. To minimize the effects of minor sample defects, sample specimens were cut parallel to the direction in which the drawdown of the cured film was prepared. If the cured film was tacky to the touch, a small amount of talc was applied to the film surface using a cotton tipped applicator.

The test specimens were then removed from the substrate. Caution was exercised so that the test specimens were not stretched past their elastic limit during the removal from the substrate. If any noticeable change in sample length had taken place during removal from the substrate, the test specimen was discarded. If the top surface of the film was talc coated to eliminate tackiness, then a small amount of talc was applied to the bottom surface of test specimen after removal from the substrate.

The average film thickness of the test specimens was determined with a micrometer. At least five measurements of film thickness were made in the area to be tested (from top to bottom) and the average value used for calculations. If any of the measured values of film thickness deviated from the average by more than 10% relative, the test specimen was discarded. Film width was also measured. All specimens came from the same plate, and generally, at least six strips were needed to obtain tensile properties.

The appropriate load cell was determined by consideration of the following equation (7):

$$[A \times 145] \times 0.0015 = C \quad (7)$$

Where: A=a product's maximum expected tensile strength (MPa); 145=Conversion Factor from MPa to psi; 0.0015= approximate cross-sectional area (in2) of test specimens; and C=lbs. The 2 pound load cell was used for materials where C=1.8 lbs. or less. The 20 pound load cell was used for materials where C was between 1.8 and 19 lbs. If C was higher than 19 lbs, a higher capacity load cell was required. Analogous steps were used for metric load cells.

The crosshead speed was set to 1.00 inch/min (or to a metric value equal to $^1\!/_2$ the gage length), and the crosshead action was set to "return at break." The crosshead was adjusted to 2.00 inches jaw separation. The air pressure for the pneumatic grips was turned on and adjusted as follows: set at approximately 20 psi (1.5 Kg/cm$^2$) for primary optical fiber coatings and other very soft coatings; set at approximately 40 psi (3 Kg/cm$^2$) for optical fiber single coats; and set at approximately 60 psi (4.5 Kg/cm$^2$) for secondary optical fiber coatings and other hard coatings. An appropriate Instron computer method was loaded for the coating to be analyzed.

After the Instron test instrument had been allowed to warm-up for fifteen minutes, it was calibrated and balanced following the manufacturer's operating procedures. The temperature near the Instron instrument was measured and the humidity was measured at the location of the humidity gage. This was done just before beginning measurement of the first test specimen.

Specimens were only analyzed if the temperature was within the range 23±2° C., and the relative humidity was within 50±5%. The temperature was verified as being within this range for each test specimen. The humidity value was verified only at the beginning and the end of testing a set of specimens from one plate.

After calibration and standardization, each test specimen was tested by suspending it into the space between the upper pneumatic grips such that the test specimen was centered laterally and hanging vertically. The upper grip (only) was locked. The lower end of the test specimen was pulled gently so that it has no slack or buckling, and it was centered laterally in the space between the open lower grips. While holding the specimen in this position, the lower grip was locked.

The sample number and sample dimensions were entered into the data system, following the instructions provided by the software package. Tensile measurement for the sample was then executed with the Instron device. This was repeated for additional specimens. The temperature and humidity were measured after the last test specimen from the current drawdown was tested.

The calculation of tensile properties was performed automatically by the software package. The values for tensile strength, % elongation, and secant modulus were checked to determine whether any one of them deviated from the average enough to be an "outlier." If necessary, the procedure was repeated.

Elastic Modulus Test Method

A dynamic mechanical analysis was also carried out on the test samples. Elastic modulus (E'), viscous modulus (E"), and tan delta (E"/E') were measured by conventional DMA methods. A free film specimen of cured material was cut to size (about 35 mm length), measured for width and thickness and mounted. The environmental chamber containing the sample was brought to 80° C. The sample was stretched before temperature sweep was started. The temperature was lowered in prescribed steps to the starting temperature. The temperature sweep was started and allowed to proceed upwards on the temperature scale until the material was beyond the glass transition range and well into the rubbery range. The DMA instrument (Rheometrics Solids Analyzer, RSA-II equipped with a personal computer) produced a plot of the data on the computer screen. The temperature at which E' is 1,000 MPa and E' is 100 MPa was calculated from this plot, as well as the tan delta peak. The minimum value of E' attained in the rubbery region was measured and reported on Tables 1 and 2 as $E_o$ (equilibrium modulus or rubbery modulus).

Aging Test for Testing of Hydrolytic Stability

Additional test samples prepared in the same manner were subjected to aging in a controlled chamber maintained at 85° C. and 85% relative humidity. After 10 days of aging under these conditions, a set of test samples was removed and tested in accordance with the above dynamic mechanical analysis procedures, and an equilibrium modulus $E_o$ determined. This value was compared to the $E_o$ prior to aging and the result is reported as the percent $E_o$ loss or change after 10 days aging relative to the initial value. A further set of samples was removed from the chamber after aging for 30 days and tested in the same manner, and the result is reported as the percent $E_o$ loss or change after 30 days aging relative to the initial value.

Thermogravimetric Analysis (TGA)

The weight losses of the cured optical fiber coating formulations were continuously monitored at elevated temperatures using thermogravimetric analysis techniques (TGA). The results were represented as a function of time at a fixed temperature. A sample of material being tested is heated in the TGA apparatus, while the weight and temperature are being continuously recorded as a function of time. The rate or magnitude of weight change is reported as a measure of thermal stability.

Heretofore, 0.254 mm drawdowns of each coating material were made and cured according to Test Method B8-2.1. Small squares of sample were cut out (typically 10 to 20 mg of material).

A Thermal Analyzer, DuPont 9900 or equivalent, is used as equipment. The TGA module balance is zeroed and tared, the balance assembly is retracted from the furnace and 10–20 mg of sample is placed in the balance pan. The balance is returned to the correct position in the furnace. The sample weight is automatically determined. An air flow to 100 cc/minute (±20 cc/min) is established through the furnace and purged for five minutes to establish equilibrium. The control and data acquisition software is initiated and the test is allowed to proceed for 40 minutes after temperature equilibrium is established (isothermal at 200° C.). At the end of the analysis, the sample is removed.

Results are provided by the software package. The accuracy of the weight measurement is ±1.0% of full scale. The precision of the weight measurement is ±0.4% of full scale.

Onset of Oxidation Temperature (or Oxidation Initiation Temperature OIT) by Thermal Analysis This method describes the use of Differential Scanning Calorimetry (DSC) to measure the onset of oxidation temperature for cured Fiber Optic Materials. A thermal scan is run, using the analyzer's DSC module, in an oxygen atmosphere. The extrapolated onset temperature is taken as a measure of thermal stability of the cured material.

One 0.254 mm drawdown is prepared per material to be tested (see Test Method B8-2.1 Preparation of Cured Films for drawdown preparation). The drawdowns are cured at a dose which is considered to provide fully cured films. A blade handle and scalpel blade is used to cut squares of cured film which will provide five to ten milligrams of sample. The squares of coating are removed, are placed in a tared sample pan, and are weighed, to the nearest 0.1 mg, using the analytical balance.

Thermal Analyzer DuPont 9900 or equivalent is used. Typical parameters chosen in the DSC software package are:

Sample Weight: 5 to 10 mg

Initial temperature: 25° C.

Final temperature: 300° C.

Heating rate: 10° C./minute flow rate.

Atmosphere: Oxygen at 50 ml/minute flow rate.

The sample is placed in the tared pan as indicated above in the DSC module's sample holder. An empty pan is placed in the DSC reference holder. The flow rate of oxygen to the DSC module at about 2 psi pressure and 50 ml/minute flow rate is started. The programmed temperature rise and data acquisition is initiated. The temperature range scanned should be 50° C. wider than the temperatures over which transitions in the sample are likely to occur. At the end of the run, the oxygen flow should be shut off. If the DSC has a provision for multiple samples, two replicates should be run simultaneously. Otherwise, the module should be cooled to the starting temperature, the first replicate removed, and the measurement repeated.

The onset of oxidation temperature is calculated from the intersection of the baseline with the tangent to the inflection point in the heat flow versus temperature curve. The onset of oxidation temperature (OIT) is reported as the average of the values obtained from duplicate analyses. The analysis should be considered suspect if the duplicate runs vary by more than ±3° C. from the average.

Cure Speed FTIR Test (%RAU)

The relative cure rates for ultraviolet cured coatings can be determined using FTIR transmission techniques. The method is applicable to coating systems that cure by loss of double bonds, in particular acrylate double bonds, when exposed to ultraviolet light.

Equipment:

A Fourier transform infrared (FTIR) spectrophotometer, Nicolet 60SX or equivalent instrument is used. Instrument parameters are: TGS detector, 4 $cm^{-1}$ resolution and ten scans are co-added for each spectrum.

Infrared spectrometry is now well known and any infrared spectrometer can be utilized to obtain the infrared spectrum.

A Mercury UV lamp, 100 W, Oriel Corp. #6281 or equivalent is used. Alternative UV lamp systems capable of producing controlled short pulses of radiation may be substituted.

Sample preparation:

A Teflon spacer is placed onto the surface of a clean NaCl transmission window. By using a tip of a disposable glass pipette, a small drop of thoroughly mixed coating is placed in the center of the NaCl disc. A second NaCl disc is placed carefully on top of the drop of coating such that the coating spreads evenly to the edge of the spacer and such that no air bubbles are present in the coating.

Instrument Set-Up/Standardization:

The UV lamp is turned on, then the FTIR is turned on. A background spectrum is collected with no sample in the IR beam path.

Procedure for Analyzing Samples:

For a first analysis of a coating system a standard procedure is followed to ensure that the coating thickness is constant for any one coating system. A 50 micron spacer is used for achieving a constant thickness. Therefore, the net absorbance of the unsaturation band from the peak minimum to the peak maximum is measured. The peak maximum should be in the 1.0 to 1.2 A range. The net absorbance will depend on the peak minimum. For coatings based on acrylate chemistry, the acrylate unsaturation band at 810 $cm^{-1}$ and a baseline at the minimum near 795 $cm^{-1}$ is used. This step is repeated three times and the average of the three absorbance values is taken as the net absorbance. This averaged value is used as a target absorbance for all future analyses of that particular coating system. This value is likely to differ for each coating system due to the differences in unsaturation content. The coating thickness is then adjusted by tightening the demountable cell holder screws until the net absorbance of the unsaturation band is within ±0.05 A of the above described averaged value for the net absorbance. Spectra are collected, one right after another, until the net absorbance value stabilizes (the coating may take a few minutes to reach equilibrium).

Then, an infrared spectrum of the uncured, liquid sample and an infrared spectrum of the cured sample are obtained by varying the exposure times between 0.05 and 5 seconds. Exposure times may vary depending on the coating system, for example, fast curing coating systems require shorter exposure times. The net peak area of the acrylate unsaturation absorbance for the uncured liquid sample is measured. For most acrylate-based coatings, the absorbance at about 810 $cm^{-1}$ should be used. However, if the coating contains a siloxane or other component which absorbs strongly at or near 810 $cm^{-1}$, an alternative acrylate absorbance peak can be used. The absorbances at about 1410 $cm^{-1}$ and about 1635 $cm^{-1}$ have been found to be satisfactory. The net peak area can be measured using the well known baseline technique in which a baseline is drawn tangent to absorbance minima on either side of the peak. The area above the baseline and under the peak is the net peak area.

A reference area is then determined. The reference absorbance should not change in intensity as the liquid sample is cured. Many formulations have an absorbance in the range of about 780 to about 750 $cm^{-1}$ that can be used as a reference absorbance. The net peak area of the reference absorbance is measured.

Both sample and reference are measured in triplicate for each exposure time.

Calculations:

The ratio of the acrylate absorbance to the reference absorbance for the uncured, liquid sample is determined using the following formula (8):

$$R_L = A_{AL}/A_{RL} \tag{8}$$

where $A_{AL}$ is the net peak area of the acrylate absorbance (under the acrylate band), $A_{RL}$ is the net peak area of the reference absorbance, and $R_L$ is the area ratio for the liquid sample.

The ratio of the acrylate absorbance to the reference absorbance for the cured sample is determined using the following formula (9):

$$R_C = A_{AC}/A_{RC} \tag{9}$$

where $A_{AC}$ is the net peak area of the acrylate absorbance, $A_{RC}$ is the net peak area of the reference absorbance, and $R_C$ is the area ratio for the cured sample.

The degree of cure as a percent reacted acrylate unsaturation (%RAU) is determined using the following formula (10):

$$\%RAU = [(R_L - R_C) \times 100\%]/R_L \tag{10}$$

The average %RAU is determined for the triplicate analyses for each time exposure for both sample and reference. The time of exposure are then plotted versus %RAU for both sample and reference.

The precision of the data used to obtain the exposure time versus %RAU plot varies over the course of the plot. At exposure times where the curve is not steep, values ±2% (absolute) of the average value are acceptable. At exposure times where the curve is very steep, values ±7% (absolute) of the average value are acceptable.

Adhesion to Secondary and Release from Matrix

To test the ink compositions, glass plates were coated with a 75 micron thick, secondary coating which was cured with a D-lamp (1 J/$cm^2$). Next, the 25 micron thick drawdowns of the ink compositions were applied to coated glass plates, and then irradiated with ultraviolet light by a combination of a D lamp with an energy of 125 mJ/cm² in the wavelength area up to 450 nm to produce cured ink films. The energy output of the D lamp was measured by a EIT UV-cure light bug. With these test plates, the adhesion of the ink to the secondary coating was determined.

In order to test the adhesion (or break-out) of the matrix material from the inks, coated and inked glass plates were used, and a 75 micron thick matrix material was coated thereon. The matrix was cured with a D-lamp at 1 J/cm².

The adhesion strength of the cured ink coating and release from the matrix material were measured using the so-called "sandwich test" or "ink adhesion test". In said test, the ink composition is applied to a secondary coating, and on top of the ink composition a matrix material was applied ("sandwich" of ink composition in between secondary coating and matrix material). The matrix was cut into with a knife and was peeled back.

The release of ink composition from the matrix material was judged. If ink peels off the secondary coating and sticks to the matrix (also when some residues of the ink remain on the matrix or vice versa), this indicated failure of the ink. If the ink remains on the secondary and releases from the matrix, the ink passes the test. The adhesion to the secondary and release from the matrix can be easily visually observed, since the ink is colored.

Method for Measuring the Acid Value AV

About 2 gram of sample is diluted in 25 ml THF. Then 1 ml water is added to dissociate the acid(s) into its (their) ions. The mixture is potentiometrically titrated with 0.1 M potassium hydroxide in methanol standard solution (KOH/MeOH) after it is stirred for 5 minutes. Both acid values (AV1, for acids having a pKa≦2, and AV2, for acids having a pKa>2) are automatically determined on a Toledo DL58 Titrator.

Further, in order to more accurately determine the strong acid value AV1, the amount of sample can be increased. The appropriate amount of sample depends on the expected acid value. Some guidelines are:

AV<1: amount sample>2 gram

1<AV<100: amount sample 0,5–2 gram

AV>100: amount sample: <0,5 gram

The acid value is automatically calculated on the basis of the formulation (11):

$$AV=(V_{eq.}*t*56.1)/m \qquad (7)$$

where: AV=Acid Value $V_{eq}$=volume (ml) titrant used in equivalence point t=titer of 0.1 n KOH m=amount of sample in gram

What is claimed is:

1. Radiation-curable coating, ink or matrix composition comprising:
    (A) a urethane-free polyester (meth)acrylate oligomer comprising a polyacid residue or anhydride thereof,
    (B) optionally, a reactive diluent, and
    (C) optionally, a photoinitiator,
wherein the composition when cured is hydrolytically stable to such an extent that the coating, ink or matrix maintains mechanical integrity when aged at 85° C. and 85% Relative Humidity for 10 days.

2. Radiation-curable coating, ink or matrix composition according to claim 1, wherein the polyester (meth)acrylate oligomer (A) comprises more than about 1 mole of diacid.

3. Composition according to claim 1, wherein the composition when cured shows a change in equilibrium modulus $E_o$ of about 30% or less when aged for 10 days under 85° C. and 85% Relative Humidity.

4. Composition according to claim 1, wherein the composition when cured shows a change in equilibrium modulus $E_o$ of about 60% or less when aged for 30 days under 85° C. and 85% Relative Humidity.

5. Composition according to claim 1, wherein the composition is a primary coating composition, after cure, having a modulus of about 5 MPa or less.

6. Composition according to claim 1, wherein the composition is a matrix composition, after cure, having a modulus of at least about 5 MPa.

7. Composition according to claim 1, wherein the composition is a secondary coating composition or an ink imposition.

8. Composition according to claim 1, wherein the composition is colored.

9. Radiation-curable coating, ink or matrix composition comprising:
    (A) a urethane-free polyester (meth)acrylate oligomer comprising a polyacid residue or anhydride thereof,
    (B) optionally, a reactive diluent, and
    (C) optionally, a photoinitiator,
wherein said composition when cured shows a weight loss of about 10% or less when submitted to 200° C. for 40 minutes in a Thermogravimetric Analysis (TGA) measurement.

10. Radiation-curable coating, ink or matrix composition comprising:
    (D) a urethane-free polyester (meth)acrylate oligomer comprising a polyacid residue or anhydride thereof,
    (E) optionally, a reactive diluent, and
    (F) optionally, a photoinitiator,
wherein said composition, in the absence of an additive or anti-oxidant, when cured shows an onset of oxidation temperature (OIT) of at least about 217° C. when submitted to Differential Scanning Calorimetry (DSC).

11. Composition according to claim 9, wherein the polyester (meth)acrylate oligomer (A) comprises more than about 1 mole of diacid.

12. Composition according to claim 1, wherein the polyester (meth)acrylate (A) is derived from
    (i) a polybasic acid chosen from the group consisting of adipic acid, isophthalic acid, terephthalic acid, dimer-fatty acid or a mixture thereof,
    (ii) a polyalcohol chosen from the group consisting of ethoxylated bisphenol-A, propoxylated bisphenol-A, neopentyl glycol, 2-butyl-2-ethyl-1,3-propanediol, 2-methyl-1,3-propanediol, hydroxy pivaloyl hydroxy pivalate, 2,4-diethyl-1,5-pentanediol or mixtures thereof and
    (iii) (meth)acrylic acid.

13. A process comprising applying the composition according to claim 1 as a primary coating, secondary coating, ink composition or matrix material on an optical glass fiber.

14. Coated and optionally inked optical fiber comprising a glass optical fiber having a primary coating, a secondary coating, and optionally an ink composition applied thereon, said coated optical fiber being adapted for use in a ribbon by encapsulating a plurality of said coated fibers in a matrix material, wherein at least one of said coating, ink composition or matrix material is derived from a radiation-curable composition according to claim 1.

15. An optical fiber ribbon comprising a plurality of coated and optionally inked optical fibers according to claim 14 held together by a matrix material.

16. The composition of claim 1, wherein said composition comprises, relative to the total weight of the composition, less than 40 wt % urethane (meth)acrylate oligomer.

17. The composition of claim 1, wherein said composition comprises, relative to the total weight of the composition, less than 25 wt % urethane (meth)acrylate oligomer.

* * * * *